United States Patent [19]

Kelley et al.

[11] Patent Number: 5,872,118
[45] Date of Patent: Feb. 16, 1999

[54] BICYCLIC AMIDE DERIVATIVES AND THEIR USE AS MUSCLE RELAXANTS

[75] Inventors: James Leroy Kelley, Raleigh; Gregory Cooksey Rigdon; Barrett Randolph Cooper, both of Durham; Ed Williams McLean; David Lee Musso, both of Raleigh; Gloria Faye Orr, Chapel Hill; Jeffrey Leaman Selph; Virgil Lee Styles, both of Durham, all of N.C.

[73] Assignee: Glaxo Wellcome Inc., Research Triangle Park, N.C.

[21] Appl. No.: 549,686

[22] PCT Filed: May 10, 1994

[86] PCT No.: PCT/GB94/01003

§ 371 Date: Dec. 18, 1995

§ 102(e) Date: Dec. 18, 1995

[87] PCT Pub. No.: WO94/26693

PCT Pub. Date: Nov. 24, 1994

[30] Foreign Application Priority Data

May 11, 1993 [GB] United Kingdom .................. 9309621

[51] Int. Cl.$^6$ .................................................. A61K 31/535
[52] U.S. Cl. ..................... 514/231.2; 514/233.5; 514/456; 514/617; 514/906; 514/825; 514/886; 544/151; 544/106; 549/398; 564/180
[58] Field of Search .......................... 584/35; 814/231.2, 814/233.5, 456, 617, 906, 805, 856; 544/106, 157; 549/398; 564/180

[56] References Cited

U.S. PATENT DOCUMENTS 4,172,093  10/1979  Göransson-Dahlander et al. .................................................................................. 260/570.8

FOREIGN PATENT DOCUMENTS

| 0281373 | 4/1987 | European Pat. Off. . |
| 218373 | 4/1987 | European Pat. Off. . |
| 2177929 | 11/1973 | France . |
| 1241438 | 6/1967 | Germany . |
| 2202729 | 8/1972 | Germany . |
| 62-273972 | 11/1987 | Japan . |

OTHER PUBLICATIONS

Ivanov et al., A New Route to Benzofulvene Derivatives, *CR Acad Bueg Sci*, 21(3), pp. 257–260, (1968).
Jönsson et al., Pharmacologically active derivatives of geminally dialkylated indenes and indans, *Acta Pharm. Suec.*, 16, pp. 173–186, (1979).
Bahl et al., Nuclear Magnetic Resonance Evidence Regarding the Stereochemistry of Some Cynaoindanylidene Compounds, *J. Chem. Soc.*, (C) pp. 1583–1584, (1971).
Popandova et al., Interaction of Aliphatic and Alicyclic Nitriles with Benzylideneacetophenone in the Presence of Lithium Amide in Liquid Ammonia *Dokl. Bolg. Akad. Nauk*, 24(5), pp. 621–624, (1971).

Eweiss et al., Knoevenagel–Type Condensation of Indan–1–One with Active Methylene Compounds, *Revue Roumaine de Chimie*, 24(11–12), pp. 1485–1489, (1979).
Bowden et al., Constituents of Eupomatia Species, IV Structure and Synthesis of Eupolauridine (El Base–1) and Some Observations on the Structures of Eupolauramine (El Base–2) and Hydroxyeupolauramine (El Base–3), *Aust. J. Chem.*, 28, pp. 2681–2701, (1975).
Brewster et al., Structure of the Indene–3–acetic Acids, Part II, Reformatsky Reactions of 6–Benzyloxy–,5, 6–Dimethoxy–, and 6–Methoxy–indan–1–ones, *Journal the Chem Soc. Perkin Trans 1*, vol. 7, pp. 941–943, (1972).
Hoffsomer et al., Structure of the Indenylacetic Acids, *Journal of Organic Chemistry*, 34(12), pp. 4182–4184, (1969).
Angehelova et al., Conversion of 5–Aryl–3–phenyl–2, 4–pentadienoic Acids and Their Amides into Indane Derivatives, *Synthesis*, pp. 116–117, (Feb. 1974).
Paull et al., A New Class of Sultones and Related Compounds, *Journal of Heterocyclic Chemistry*, 10(1), pp. 137–138, (Feb. 1973).

*Primary Examiner*—Gary Geist
*Assistant Examiner*—Deborah D. Carr
*Attorney, Agent, or Firm*—Shah R. Makujina

[57] ABSTRACT

Novel compounds of formula (I)

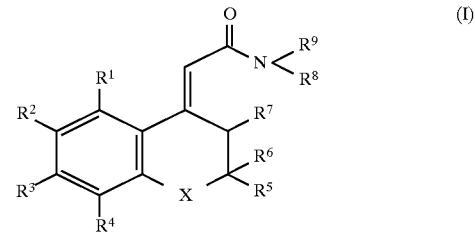

wherein
$R^1$, $R^2$, $R^3$ and $R^4$ are each selected from hydrogen and fluoro and at least one and not more than two is fluoro;
$R^5$ is selected from hydrogen and $C_1$–$C_4$ alkyl;
$R^6$ is selected from hydrogen, $C_1$–$C_4$ ally and hydroxy; or
$R^5$ and $R^6$ together with the ring carbon form a carbonyl group;
$R^7$ is selected from hydrogen and hydroxy,
$R^8$ and $R^9$ are each selected from hydrogen, $C_1$–$C_4$ alkyl and cyclo($C_3$ or $C_4$) alkyl or together with the nitrogen form a morpholino group; and
X is selected from a bond, methylene and —O— and is always a bond or —O— when any of $R^5$, $R^6$ and $R^7$ is other than hydrogen and is always a bond when $R^5$ and $R^6$ together with the ring carbon form a carbonyl group;
and their salts and solvates have a number of uses as central muscle relaxants. In particular, treatment of conditions associated with abnormally raised skeletal muscle tone. They are of special value in the relaxation of skeletal muscle in spastic, hypertonic and hyperkinetic conditions.

9 Claims, No Drawings

BICYCLIC AMIDE DERIVATIVES AND THEIR USE AS MUSCLE RELAXANTS

This application is a 371 of PCT/GB94/01003 filed May 10, 1994.

The present invention relates to amide compounds, synthesis thereof, intermediates, salts and solvates thereof, pharmaceutical compositions containing them and the use of such compounds and compositions in medicine and therapy, particularly as central muscle relaxants.

The major limiting side effects of many clinically effective central muscle relaxants and anticonvulsants are the induction of sedation and incoordination in the recipient, which severely limit their usefulness. Similar side effects are found with drugs used in the treatment of anxiety, such as benzodiazepines. Although these effects may be transient, patients on such therapy are often unable to drive or participate in certain occupations.

It has now surprisingly been found that amides of formula (I) are potent central muscle relaxants and have a significantly reduced liability to sedation and incoordination compared with known agents.

In one aspect the present invention provides the novel compounds of formula (I)

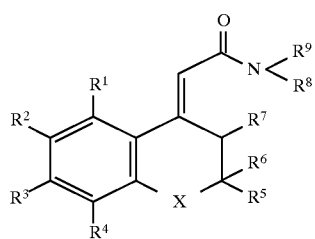

wherein
$R^1$, $R^2$, $R^3$ and $R^4$ are each selected from hydrogen and fluoro and at least one and not more than two is fluoro;
$R^5$ is selected from hydrogen and $C_1$–$C_4$ alkyl;
$R^6$ is selected from hydrogen, $C_1$–$C_4$ alkyl and hydroxy; or
$R^5$ and $R^6$ together with the ring carbon form a carbonyl group;
$R^7$ is selected from hydrogen and hydroxy;
$R^8$ and $R^9$ are each selected from hydrogen, $C_1$–$C_4$ alkyl and cyclo($C_3$ or $C_4$)alkyl or together with the nitrogen form a morpholino group; and
X is selected from a bond, methylene and —O— and is always a bond or —O— when any of $R^5$, $R^6$ and $R^7$ is other than hydrogen and is always a bond when $R^5$ and $R^6$ together with the ring carbon form a carbonyl group;
and salts and solvates thereof.

As used herein,
"$C_1$–$C_4$ alkyl" means a linear or branched chain alkyl group having 1, 2, 3 or 4 carbon atoms;
"cyclo($C_3$ or $C_4$)alkyl" means a cycloalkyl group having 3 or 4 carbon atoms;
"salts" means base salts formed when, in formula (I), one of $R^8$ and $R^9$ is hydrogen; and
"solvates" means a combination, in definite proportions, of a compound of formula (I) and a solvent therefor.

It will be appreciated that the compounds of formula (I) can exist in various geoisomeric forms and as mixtures thereof in any proportions. The present invention includes within its scope such geoisomeric forms or mixtures of geoisomers, including the individual E and Z isomers of the compounds of formula (I) as well as mixtures of such isomers, in any proportions.

Included within formula (I) are compounds wherein one or more carbon centers is/are chiral. The present invention includes within its scope each possible optical isomer substantially free from, i.e., associated with less than 5% of, any other optical isomer(s), as well as mixtures of one or more optical isomers in any proportions, including racemic mixtures thereof.

It will be evident to a skilled person that certain compounds of formula (I) can exist in enantiomeric forms according to the direction of rotation of plane polarized light when passed through a sample of the compound. Individual optical isomers as well as mixtures of such isomers in any proportions are within the scope of the invention.

As will be appreciated, structural formula (I) is merely a two-dimensional representation of the compounds.

Separate groups of compounds, within formula (I), include those wherein
(i) one of $R^1$, $R^2$, $R^3$ and $R^4$ is fluoro;
(ii) two of $R^1$, $R^2$, $R^3$ and $R^4$ are fluoro;
(iii) $R^1$ is fluoro;
(iv) $R^2$ is fluoro;
(v) $R^3$ is fluoro;
(vi) $R^4$ is fluoro;
(vii) $R^5$ is hydrogen;
(viii) $R^5$ is $C_1$–$C_4$ alkyl, preferably alkyl having 1, 2 or 3 carbon atoms and more preferably methyl or ethyl;
(ix) $R^6$ is hydrogen;
(x) $R^6$ is $C_1$–$C_4$ alkyl, preferably alkyl having 1, 2 or 3 carbon atoms and more preferably methyl or ethyl;
(xi) $R^6$ is hydroxy;
(xii) $R^5$ and $R^6$ together with the ring carbon form a carbonyl group;
(xiii) $R^7$ is hydrogen;
(xiv) $R^7$ is hydroxy;
(xv) $R^8$ is hydrogen;
(xvi) $R^8$ is $C_1$–$C_4$ alkyl, preferably alkyl having 1, 2 or 3 carbon atoms and more preferably methyl, ethyl or isopropyl;
(xvii) $R^8$ is cyclo($C_3$ or $C_4$)alkyl, preferably cyclopropyl;
(xviii) $R^9$ is hydrogen;
(ix) $R^9$ is $C_1$–$C_4$ alkyl, preferably alkyl having 1, 2 or 3 carbon atoms and more preferably methyl, ethyl or isopropyl;
(xx) $R^9$ is cyclo($C_3$ or $C_4$)alkyl, preferably cyclopropyl;
(xxi) $R^8$ and $R^9$ together with the nitrogen form a morpholino group;
(xxii) X is a bond;
(xxiii) X is methylene;
(xxiv) X is —O—;
and salts and solvates thereof.

Preferred as a class are compounds wherein the >C═O group and the benzene ring are on opposite sides of the exo double bond, and salts and solvates thereof.

Individual preferred compounds within formula (I) include
(E)-2-(6-fluoro-3-methyl-1-indanylidene)acetamide;
(E)-N-cyclopropyl-2-(6-fluoro-3-methyl-1-indanylidene) acetamide;
(E)-2-(6-fluoro-3,3-dimethyl-1-indanylidene)-N-methylacetamide;
(E)-N-cyclopropyl-2-(6-fluoro-3-ethyl-1-indanylidene) acetamide;

(E)-N-cyclopropyl-2-(5,6-difluoro-1-indanylidene) acetamide;
(E)-2-(5,6-difluoro-1-indanylidene)-N-methylacetamide;
(E)-2-(5,6-difluoro-1-indanylidene)acetamide;
(E)-2-(5,7-difluoro-1-indanylidene)acetamide;
(E)-N-cyclopropyl-2-4,6-difluoro-1-indanylidene) acetamide;
(E)-2-(4,6-difluoro-1-indanylidene)-N-isopropylacetamide;
(E)-2-(4,6-difluoro-1-indanylidene)-N,N-dimethylacetamide;
(Z)-2-(4,6-difluoro-2-hydroxy-1-indanylidene)acetamide;
(E)-2-(7-fluoro-1,2,3,4-tetrahydro-1-naphthylidene) acetamide;
(E)-N-cyclopropyl-2-(7-fluoro-1,2,3,4-tetrahydro-1-naphthylidene)acetamide;
(E)-N-cyclopropyl-2-(6-fluoro-3,4-dihydro-2H-1-benzopyran-4-ylidene)acetamide;
(E)-2-(4,6-difluoro-1-indanylidene)acetamide;
(E)-2-(6-fluoro-1-indanylidene)acetamide;
(Z)-2-(6-fluoro-2-hydroxy-1-indanylidene)acetamide;
(E)-2-(6-fluoro-3,3-dimethyl-1-indanylidene)acetamide;
(E)-2-(6-fluoro-3-ethyl-1-indanylidene)-N,N-dimethylacetamide;
(E)-2-(6-fluoro-3-hydroxy-1-indanylidene)acetamide
and salts and solvates thereof.

Particularly preferred is (E)-2-(4,6-difluoro-1-indanylidene)acetamide, together with its salts and solvates.

Preferred salts and solvates are those that are pharmaceutically acceptable.

The present invention further provides a compound of formula (I), or a pharmaceutically acceptable salt or solvate thereof, for use in the medical treatment of a mammal including a human being.

The present invention also provides the use of a compound of formula (I), or a pharmaceutically acceptable salt or solvate thereof, for the manufacture of a medicament for the medical treatment of a mammal including a human being.

The pharmaceutically acceptable salts include ammonium salts; alkali metal salts, for example sodium and potassium salts; and alkaline earth metal salts, for example magnesium and calcium salts.

Salts that are not pharmaceutically acceptable have utility in the preparation and/or purification of the compounds themselves and/or of those salts thereof that are acceptable, and/or in non-therapeutic, for example in vitro, applications.

The compounds of formula (I) together with their pharmaceutically acceptable salts and solvates are useful in medicine as central muscle relaxants and may thus be used in the treatment of conditions associated with abnormally raised skeletal muscle tone.

They are of especial value in the relaxation of skeletal muscle in spastic, hypertonic and hyperkinetic conditions. In particular, they may be used in the treatment and symptomatic relief of exertion-induced skeletal muscle spasm, for example, in lower back pain. They may also be used in conditions such as spinal cord injury, parkinsonism, chorea, arthritis, athetosis, status epilepticus and tetanus and especially in the relief of muscle spasm in conditions such as spasticity, myositis, spondylitis, cerebral palsy, cerebrovascular disease and multiple sclerosis. They may also be used as pre-surgical muscle relaxants.

Compounds of formula (I) together with their pharmaceutically acceptable salts and solvates are also useful in the treatment of conditions associated with a convulsive state, for example that following grand mal, petit mal, psychomotor epilepsy or focal seizure.

Compounds of formula (I) together with their pharmaceutically acceptable, salts and solvates are also useful in the treatment of anxiety; as used herein, this term should be understood to include anxiety disorders.

Anxiety disorders are defined, in the Diagnostic and Statistical Manual of Mental Disorders (Third Edition—Revised, 1987, published by the American Psychiatric Association, Washington, D.C., U.S.A., see pages 235 to 253), as psychiatric conditions having symptoms of anxiety and avoidance behaviour as characteristic features. Included amongst such conditions are generalised anxiety disorder, simple phobia and panic disorder.

Anxiety also occurs as a symptom associated with other psychiatric disorders, for example obsessive compulsive disorder, post-traumatic stress disorder, schizophrenia, mood disorders and major depressive disorders, and with organic clinical conditions such as Parkinson's disease, multiple sclerosis and other physically incapacitating disorders.

Compounds of formula (I) together with their pharmaceutically acceptable salts and solvates are also useful in the treatment of pain, for example that associated with inflammation and/or trauma, and have utility as mild and strong analgesics.

Compounds of formula (I) together with their pharmaceutically acceptable salts and solvates are also useful in the treatment of inflammatory conditions including inflammatory arthritic conditions, for example rheumatoid arthritis, rheumatoid spondylitis, osteoarthritis and gouty arthritis; and non-articular inflammatory conditions, for example herniated/ruptured/prolapsed intervertebral disk syndrome, bursitis, tendinitis, tenosynovitis, fibromyalgia syndrome and other inflammatory conditions associated with ligamentous sprain and regional musculoskeletal strain. It is particularly notable that they are less ulcerogenic than other anti-inflammatory agents such as ibuprofen, naproxen and aspirin.

The present invention thus also provides a method for the treatment of
  a) a condition associated with abnormally raised skeletal muscle tone;
  b) a condition associated with a convulsive state;
  c) anxiety;
  d) pain; or
  e) an inflammatory condition
in a mammal including a human being, the method comprising administering thereto a therapeutically effective amount of a compound of formula (I) or a pharmaceutically acceptable salt or solvate thereof The compounds of formula (I) and their pharmaceutically acceptable salts and solvates may be administered concomitantly with other therapeutic agents for the treatment of the above-recited conditions. For conditions associated with abnormally raised skeletal muscle tone, such other agents include analgesics such as codeine, acetaminophen, phenacetin and ibuprofen. For inflammatory conditions (for example, arthritis) and/or pain, such other agents include analgesics, such as codeine, oxycodone, acetaminophen, phenacetin and ibuprofen; anti-arthritics, such as methotrexate and azathioprine; and decongestants, such as ephedrine and pseudoephedrine.

The compound, salt or solvate (hereinafter together referred to as the active ingredient) may be administered by any suitable route including oral, rectal, nasal, topical (including buccal and sublingual), vaginal, parenteral (including subcutaneous, intramuscular, intravenous and intradermal) and transdermal. It will be appreciated that the preferred route will be determined by, for example, the condition and age of the recipient and the identity of the condition to be treated.

The amount required of the active ingredient depends upon a number of factors including the identity of the condition and its severity, the identity of the recipient and the route of administration and will ultimately be at the discretion of the attendant physician.

In general, for each of the above-recited conditions, a suitable dose of the active ingredient (estimated as the parent compound) is in the range of 0.05 to 100 mg per kilogram body weight of the recipient per day, preferably in the range of 0.1 to 50 mg per kilogram body weight per day, most preferably in the range of 0.5 to 20 mg per kilogram body weight per day and optimally 1 to 10 mg per kilogram body weight per day. The desired dose is preferably presented as two, three, four, five, six or more sub-doses administered at appropriate intervals throughout the day.

While it is possible for the active ingredient to be administered alone it is preferable to present it as a pharmaceutical composition comprising an active ingredient, as defined above, together with an acceptable carrier therefor. Each carrier must be "acceptable" in the sense of being compatible with the other ingredients of the composition and not injurious to the recipient.

The compositions include those suitable for oral, rectal, nasal, topical (including buccal and sublingual), vaginal, parenteral (including subcutaneous, intramuscular, intravenous and intradermal) or transdermal administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for oral use as described above may also include buffering agents designed to neutralize stomach acidity. Such buffers may be chosen from a variety of organic or inorganic agents such as weak acids or bases admixed with their conjugated salts.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration may be presented as a suppository with a suitable base comprising for example cocoa butter or a salicylate.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the compositions isotonic with the blood of the intended recipient; and aqueous and non-aqueous sterile suspensions which may include suspending agents and thickening agents, as liposomes or other microparticulate systems which are designed to target the compounds to blood components or one or more organs. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for transdermal administration may be presented as discrete patches adapted to remain in intimate contact with the epidermis of the recipient for a prolonged period of time. Such patches suitably contain the active ingredient as an optionally buffered, aqueous solution of, for example, 0.1 to 0.2M concentration with respect to the said compound. As one particular possibility, the active ingredient may be delivered from the patch by iontophoresis as generally described in *Pharmaceutical Research,* 3(6), 318 (1986).

Preferred unit dosage compositions are those containing a daily dose or unit, daily sub-dose, or an appropriate fraction thereof, of active ingredient, for example 1 to 1500 mg, preferably 5 to 1000 mg and most preferably 10 to 700 mg of active ingredient, estimated as the parent compound.

It should be understood that in addition to the ingredients particularly mentioned above the compositions of this invention may include other agents conventional in the art having regard to the type of composition in question, for example, those suitable for oral administration may include such further agents as sweeteners, thickeners and flavouring agents.

The present invention thus also provides a pharmaceutical composition comprising a compound of formula (I) or a pharmaceutically acceptable salt or solvate thereof together with an acceptable carrier therefor.

The compounds of formula (I) and their salts and solvates may be prepared in any manner known in the art for the preparation of compounds of analogous structure, for example, in accordance with the present invention, by those methods hereinafter described.

The compounds, salts and solvates may thus be prepared by a process which comprises:
reacting a compound of formula (II)

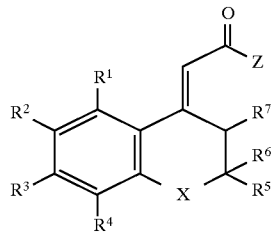

wherein $R^1$ to $R^7$ and X are as hereinbefore defined and Z is a leaving group with an amine $NR^8R^9$ or a suitable derivative thereof. Suitable leaving groups include halogen atoms such as chlorine or bromine, activated esters(e.g., N-hydroxysuccinimide, pentafluoro- phenyl, nitrophenyl, 1-hydroxybenzotriazole), mixed anhydrides(e.g., ethoxycarbonyloxy) or $C_{1-6}$ alkoxy (for example, ethoxy). The reaction is suitably carried out in an inert organic solvent(e.g., dichloromethane) at a temperature of about −20° C. −120° C., and conveniently at about 0° to 25° C. Suitable derivatives of the amine include hydrated and hydrochloride derivatives, e.g. $NH_4OH$, $NH_4Cl$.

When $R^8$ and $R^9$ are H the compounds of formula (I) can be prepared by reacting compounds of formula (II) wherein X is a halogen atom such as chlorine or bromine with the amine in hydrated form, e.g. $NH_4OH$, in a suitable organic solvent(e.g., dichloromethane) at a temperature of about 0° C. to 25° C.

Compounds of formula(I) wherein $R^6$ or $R^7$ are hydroxy can be prepared by reacting compounds of formula (II) wherein X is $C_{1-6}$ alkoxy, for example, ethoxy, and the hydroxy group is suitably protected, for example by $SiMe_2t$—Bu, with the amine present as the hydrochloride, e.g. $NH_4Cl$ in the presence of $Me_3Al$ under neutral conditions followed by deprotection under neutral conditions with, for example, pyridinium para-toulenesulfonate(PPTS).

Alternatively, compounds of formula (I) wherein $R^6$ or $R^7$ are hydroxy can be prepared from compounds of formula (I) wherein $R^6$ or $R^7$ are H by halogenation with, for example, N-bromosuccinamide(NBS) followed by hydrolysis with, for example, silver carbonate ($AgCO_3$). Compounds of formula (I) wherein the $R^6$ or $R^7$ is/are allylic hydroxy can be prepared from compounds of formula (I) wherein $R^6$ or $R^7$ are H by oxidation with, for example selenium dioxide.

Compounds of formula (II) wherein Z is a halogen atom can be prepared from compounds of formula (III)

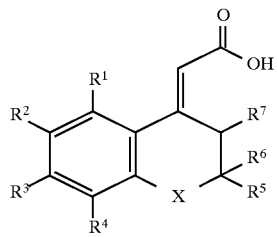

wherein $R^1$–$R^7$ and X are as hereinbefore defined by reaction with a halogenating agent(e.g., oxalyl chloride, or thionyl chloride) in a suitable organic solvent(e.g., benzene, toluene, dichloromethane) optionally in the presence of a catalyst(for example DMF)at a temperature of about −20° C. to the reflux temperature.

Compounds of formula (II) wherein Z is alkoxy(e.g., ethoxy) can be prepared from compounds of formula (III) by reaction with a suitable polar solvent (e.g., an organic alcohol such as ethanol) optionally in the presence of a catalytic amount of an acid(e.g., tosic acid) at a temperature of about 0° C. to the reflux temperature.

Compounds of formula (II) wherein Z is an activated ester(as described hereinbefore) can be prepared from compounds of formula (III) by reaction with the phenol or N-hydroxy compound and a carbodiimide(e.g., dicyclohexylcarbodiimide or 1-(3-dimethylaminopropyl)-3-ethylcarbodiimide) in a solvent such as dimethylformamide (DMF) or dichloromethane at 0° C. to 50° C.

Compounds of formula (III) can be prepared by dehydration of compounds of formula (IV) (IV)

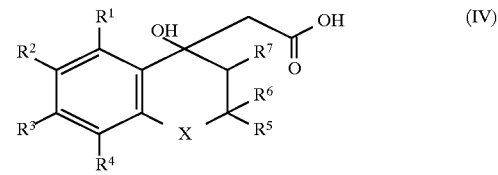

wherein $R^1$–$R^7$ and X are as hereinbefore defined by reaction with an appropriate dehydrating agent(e.g., an acid such as trifluoroacetic acid) in a suitable organic solvent(e.g., dichloromethane) at a temperature of about −20° C. to the reflux temperature.

Compounds of formula (IV) can be prepared by saponification of the corresponding $C_{1-6}$ alkyl ester, with a base (e.g., sodium hydroxide) in a suitable polar solvent(e.g., ethanol) at a temperature of about 0° C. to the reflux temperature or with an aqueous acid(e.g., hydrochloric acid) at a temperature of about 0° C. to the reflux temperature.

Esters of compounds of formula (IV) having $R^6$ or $R^7$ as protected hydroxy groups, for example, by $SiMe_2t$-Bu, can be dehydrated under neutral conditions(e.g., Martin Sulfurane, bis[α,α-bis(trifluoromethyl) benzenemethanolato]-diphenylsulfur) to give the corresponding protected hydroxy compounds of formula (II) and wherein Z is $C_{1-6}$ alkoxy(e.g., ethoxy).

The esters of compounds of formula (IV) can be prepared from compounds of formula (V)

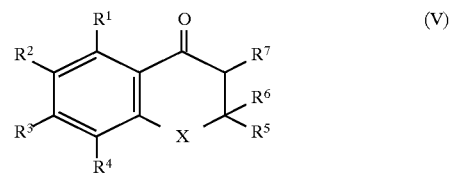

wherein $R^1$–$R^7$ and X are as hereinbefore defined by reaction with hal $CH_2CO_2R$ wherein hal is a halogen atom such as chlorine, bromine, or iodine(preferably bromine), and R is $C_{1-6}$ alkyl, (eg ethyl) in the presence of a metal(e.g., zinc, preferably activated zinc) and a catalytic amount of halogen (e.g., iodine) in a suitable organic solvent(e.g., ethyl ether, benzene) at a temperature of about 0° C. to the reflux temperature or by reaction with the lithium salt of ethyl acetate in a suitable solvent(e.g., tetrahydrofuran) at a temperature between −100° C. to room temperature(e.g., −80° C. to −70° C.).

Compounds of formula(V) having $R^6$ or $R^7$ as protected hydroxy groups as defined above can be prepared from the corresponding unprotected hydroxy compound of formula (V) by suitable protection under neutral conditions with, for example, t-butyl-di-methylsilyl chloride in the presence of a base such as imidazole.

Compounds of formula(V) having $R^6$ or $R^7$ as hydroxy can be prepared from the corresponding halogen(e.g., bromo) compound by hydrolysis under neutral conditions with, for example, silver carbonate($AgCO_3$).

Compounds of formula(V) having $R^6$ or $R^7$ as allylic alkyl(e.g., methyl) can be prepared from the corresponding compounds of formula(V) wherein $R^6$ and/or $R^7$ are H by reaction with a base(e.g., sodium hydride) followed by alkylation with, for example, methyl iodide(MeI).

Compounds of formula (V) can be prepared from compounds of formula (VI)

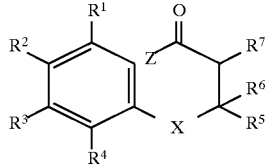
(VI)

wherein $R^1$–$R^7$, X and Z are as hereinbefore defined, preferably Z is a halogen atom such as chlorine by cyclization in the presence of a lewis acid(e.g., aluminum chloride) in a suitable solvent(e.g., dichloromethane) at a temperature of about 0° C. to the reflux temperature.

Compounds of formula (VI) wherein Z is a halogen atom(e.g., chlorine, or bromine) can be prepared from the corresponding carboxylic acid by reaction with a halogenating agent(e.g., oxalyl chloride or thionyl chloride) either neat or in a suitable organic solvent(e.g. methylene chloride or N,N-dimethylformamide) at a temperature of about 0° C. to the reflux temperature.

Compounds of formula (VI) wherein Z is alkoxy(e.g., ethoxy) can be prepared from compounds of formula (VII)

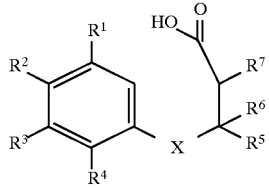
(VII)

wherein $R^1$–$R^7$ and X are as hereinbefore defined by reaction with a suitable organic alcohol (e.g., ethanol) optionally in the presence of a catalytic amount of an acid(e.g., tosic acid) at a temperature of about 0° C. to the reflux temperature.

The carboxylic acids can be prepared by saponification of the corresponding $C_{1-6}$ alkyl ester compounds with a base (e.g., sodium hydroxide) in a suitable polar solvent(e.g., water or ethanol) at a temperature of about 0° C. to the reflux temperature or with an aqueous acid (e.g., hydrochloric acid) at a temperature of about 0° C. to the reflux temperature.

The carboxyclic acids wherein X is other than oxygen can be prepared from compounds of formula (VIII)

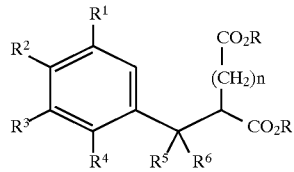
(VIII)

wherein R and $R^1$–$R^6$ are as hereinbefore defined and n is 0 or 1 by mono de-esterification with strong base(e.g., aqueous potassium hydroxide) at the reflux temperature.

Compounds of formula (VII) can be prepared by reacting a compound of formula (IX) with a compound of formula (X)

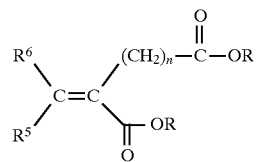
(IX)

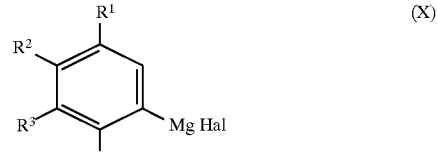
(X)

wherein R, $R^1$–$R^6$ and n are as hereinbefore defined and Hal is Cl, Br or I preferably Br in an organic solvent(e.g., anhydrous diethyl ether) and optionally in the presence of a copper halide(e.g., copper (I) iodide) at a temperature of between –50° C. to the reflux temperature.

Compounds of formula (IX) can be prepared by reacting a compound of formula (XI) with a compound of formula (XII)

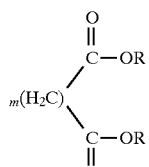
(XI)

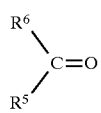
(XII)

wherein R, $R^5$ and $R^6$ are as hereinbefore defined and m is 1 or 2 in an organic solvent(e.g., ethyl ether or dichloromethane) at a temperature of between room temperature and the reflux temperature.

Compounds of formula (X) can be prepared from the corresponding halo(e.g., bromo, chloro) compound by standard techniques well known to those skilled in the art. The halo compounds themselves can be obtained commercially or or prepared by methods well known to those skilled in the art or obtainable from the chemical literature.

Alternatively, compounds of formula (IX) can be prepared according to the procedure of E. L. Eliel, R. O. Hutchins, and Sr. M. Knoeber, Organic Synthesis Coll. Vol. VI, 442, 1988 with the appropriate modifications readily apparent to those skilled in the art.

Compounds of formula (XI), and (XII) can be obtained commercially or by techniques well known to those skilled in the art or readily obtainable from the chemical literature.

Alternatively the esters can be prepared from compounds of formula (XIII)

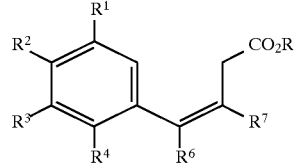
(XIII)

wherein R, $R^1$–$R^4$, $R^6$ and $R^7$ are as hereinbefore defined by reduction of the double bond, e.g., by catalytic reduction with e.g., platinum oxide($PtO_2$) and hydrogen, in a suitable organic solvent(e.g., ethanol) at a temperature of about 20° C. to 60° C.

When X is oxygen, the esters can be prepared by reacting a compound of formula (XIV) with a compound of formula (XV)

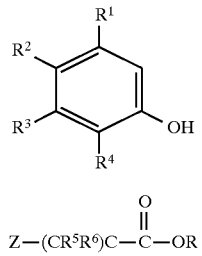
(XIV)

(XV)

wherein R, $R^1$–$R^6$ and Z are as hereinbefore defined, in a suitable organic solvent in the presence of a base(e.g., sodium hydride).

Compounds of formula (XIV) and (XV) can be obtained commercially or by methods well known to those skilled in the art or readily obtainable from the chemical literature.

Compounds of formula (XIII) can be prepared from compounds of formula (XVI)

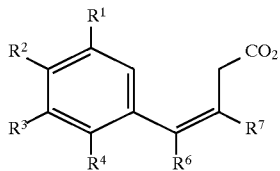
(XVI)

wherein $R^1$–$R^4$, $R^6$ and $R^7$ are as hereinbefore defined by esterification with an appropriate organic alcohol(e.g., ethanol) optionally in the presense of a catalytic amount of an acid(e.g., HCl, tosic acid, thionyl chloride)at a temperature of about 20° C. to 60° C.

Compounds of formula (XVI) can also be used to directly prepare the corresponding unsaturated acid by reduction of the double bond, e.g., by catalytic reduction with e.g., palladium or platinum oxide($PtO_2$) and hydrogen, in a suitable organic solvent(e.g., ethanol) at a temperature of about 0° C. to the reflux temperature.

Compounds of formula (XVI) can be prepared from compounds of formula (XVII)

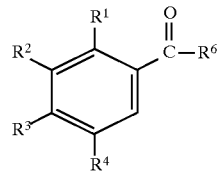
(XVII)

wherein $R^1$–$R^4$ and $R^6$ are as hereinbefore defined by reaction with $HOOCCHR^7COOH$ in an organic base(e.g., pyridine) optionally in an organic solvent(e.g., dichloromethane) optionally in a catalytic amount of a base(e.g., piperidine) at a temperature of about 0° C. to the reflux temperature.

Compounds of formula (XVII) and $HOOCCHR^7COOH$ can be obtained commercially or by methods well known to those skilled in the art or readily obtainable from the chemical literature.

Alternatively, compounds of formula (I) can be prepared by reacting $R^8R^9NCOCH_2PO(OR)_2$ (wherein R,$R^8$,$R^9$ are as hereinbefore defined) with a base (e.g., NaH) in a suitable organic solvent (e.g., THF or DMSO) and reacting the resultant anionic species with a compound of formula (VI) or (VIa) respectively at a temperature of about 0° C. to the reflux temperature. The addition of a anionic stablizing reagent (e.g., potassium hexamethyldisilizane or a crown ether (e.g., 15-crown-5) can aid the reaction.

The compound $R^8R^9NCOCH_2PO(OR)_2$ can, depending on R, $R^8$ and $R^9$ be obtained commercially or by methods well known to those skilled in the art or readily obtainable from the chemical literature. Alternatively, these compounds can be prepared by reacting the appropriate $R^8R^9NCOCH_2Z$ (wherein Z is as hereinbefore defined) with the appropriate $P(OR)_3$ in a suitable organic solvent (e.g., THF) at a temperature of about 0° C. to 50° C.

The compound $R^8R^9NCOCH_2Z$ can be prepared by reacting the appropriate $R^8R^9NH$ with $ZCH_2COZ$ in a suitable organic solvent (e.g., diethyl ether) at a temperature of about 0° C. to the reflux temperature.

The compound $R^8R^9NH$ can be obtained commercially or by methods well known to those skilled in the art of preparing amines or readily obtainable from the chemical literature. The compound $ZCH_2COZ$ can be obtained commercially or by methods well known to those skilled in the art of preparing such compounds or readily obtainable from the chemical literature.

Alternatively, compounds of formula (I) can be prepared by reacting $R^8R^9NCOCH_2P(^+)(Ph)_3Cl(^-)$(wherein $R^8$, $R^9$ and Z are as hereinbefore defined and Ph is phenyl) with a suitable base (e.g., NaH) in a suitable organic solvent (e.g., dimethoxyethane) at a temperature of about 0° C. to 50° C., and reacting the resultant anionic species with a compound of formula (V) at a temperature of about 0° C. to the reflux temperature.

The compound $R^8R^9NCOCH_2P(^+)(Ph)_3Cl(^-)$ can be prepared by reacting the appropriate $R^8R^4NCOCH_2Z$ with about a 50% molar excess of $P(Ph)_3$ (triphenylphosphine) in a suitable organic solvent (e.g., THF) at a temperature of about 20° C. to the reflux temperature.

$R^8R^9NCOCH_2Z$ can be prepared as defined hereinbefore.

Alternatively, compounds of formula (I) can also be prepared directly from compounds of formula (III) by reaction with a suitable coupling reagent (e.g., dicyclohexylcarbodiimide (DCC) or ethyl chloroformate) followed by reaction of the activated ester thus formed with the appropriate amine, $HNR^8R^9$.

Alternatively, compounds of formula (I) wherein $R^5$ is hydrogen and $R^6$ is hydroxy can be prepared from compounds of formula (I) wherein $R^5$ and $R^6$ together form a carbonyl group by reduction of this carbonyl group using a suitable reducing agent, e.g. sodium borohydride in a suitable solvent such as an alkanol (e.g. ethanol).

The compounds of formula (I) as well as any of the intermediates used in the preparation of these compounds can be effected with one or more of the following optional conversions:

(i) converting a compound of formula (I) or intermediates thereof so formed into salts thereof;

(ii) when a salt of a compound of formula (I) or an intermediate thereof is formed, converting the said salt into a compound of formula (I) or an intermediate thereof.

The following Examples illustrate the present invention but should not be construed as a limitation to the scope thereof.

EXAMPLE 1

Preparation of (E)-2-(6-Fluoro-1-indanylidene) acetamide a) Preparation of 3-(4-Fluorophenyl)propionic Acid A mixture of 4-fluorocinnamic acid (300.0 g, 1.8 mol, Aldrich) and 5% palladium on carbon (9.0 g) in ethanol (3

L) was hydrogenated at atmospheric pressure and room temperature for 4.5 h. The mixture was filtered through Celite (diatomaceous earth) and the filtrate was concentrated in vacuo to give 275.1 g (91%) of 3-(4-fluorophenyl) propionic acid as a white solid: m.p., 86°–88° C.;

b) Preparation of 3-(4-Fluorophenyl)propionyl Chloride

A mixture of 3-(4-fluorophenyl)propionic acid (275.1 g, 1.6 mol) and thionyl chloride (300 mL, 4.1 mol) was heated to reflux for 3 h, cooled to room temperature and distilled under aspirator vacuum to give 287.6 g (96%) of 3-(4-fluorophenyl)propionyl chloride as a pale pink oil, b.p., 120°–122° C./15 mm Hg:

c) Preparation of 6-Fluoro-1-indanone

A solution of 3-(4-fluorophenyl)propionyl chloride (287.6 g, 1.5 mol) in dichloromethane (1.4 L) was added dropwise during 3 h to an ice-cold, mechanically stirred suspension of aluminum chloride (226.0 g, 1.7 mol, Aldrich) in dichloromethane (2.2 L) under nitrogen. The resulting yellowish-black solution was refluxed for 5 h and allowed to cool to room temperature. The solution was washed successively with water (2 L), 1N sodium hydroxide (2 L), water (2 L) and brine (2 L). The organic layer was dried over anhydrous sodium sulfate, filtered and concentrated to a tan solid (229.1 g, 99%). The solid was recrystallized from dichloromethane-hexane to give 215.7 g (93%) of 6-fluoro-1-indanone as off-white crystals, m.p., 57°–59° C.;

d) Preparation of Ethyl 2-(6-Fluoro-1-hydroxy-1-indanyl) acetate (i) A mixture of 6-fluoro-1-indanone (5.0 g, 33.3 mmol), ethyl bromoacetate (8.3 g, 50.0 mmol, Aldrich), activated zinc powder (3.2 g, 50.0 mmol, Mallinckrodt; Org. Synth., Coll. Vol. 6, 290, 1988) and a few crystals of iodine in diethyl ether-benzene (1:1, 100 mL) was heated at reflux under nitrogen for 24 h. The mixture was filtered and the filtrate was concentrated in vacuo. The residue in diethyl ether was vigorously stirred with excess dilute ammonium hydroxide, dried and concentrated to give ethyl 2-(6-fluoro-1-hydroxy-1-indanyl) acetate as an amber oil (7.6 g, 97%);

(ii) Ethyl acetate (1.8 g, 20 mmol) was added dropwise to a stirred, chilled (dry ice-acetone bath) IN solution of lithium bis(trimethylsilyl)amide in tetrahydrofuran (20 mL, Aldrich) under nitrogen. After 15 min, a solution of 6-fluoro-1-indanone (3.0 g, 20 mmol) in tetrahydrofuran (20 mL) was added dropwise and the resulting mixture was stirred for 1 h (dry ice-acetone bath). A IN solution of hydrochloric acid (20 mL) was added and the mixture was allowed to warm to room temperature. The organic phase was separated, dried over anhydrous sodium sulfate, filtered and concentrated to a pale yellow oil (5.3 g). The mixture was chromatographed on Silica Gel 60 (silica gel) using a linear gradient of dichloromethane- hexanes (1:1) to dichloromethane as eluent. The fractions containing only ethyl 2-(6fluoro-1-hydroxy-1-indanyl)acetate were combined and concentrated in vacuo to give 3.1 g (65%) of a colorless oil:

e) Preparation of 2-(6-Fluoro-1-hydroxy-1-indanyl)acetic Acid

A mixture of ethyl 2-(6-fluoro-1-hydroxy-1-indanyl) acetate (44.0 g, 0.18 mol), 1N sodium hydroxide (180 mL) and absolute ethanol (280 mL) was stirred for 18 h at room temperature. The mixture was concentrated in vacuo, diluted with H$_2$O and extracted with diethyl ether. The aqueous phase was acidified (pH 3) with dilute hydrochloric acid and extracted with diethyl ether. The diethyl ether layer was washed with brine, dried over sodium sulfate, filtered and concentrated in vacuo to give 2-(6-fluoro-1-hydroxy-1-indanyl)acetic acid as an amber oil (37.7 g, 100%; Note: This compound spontaneously dehydrated upon standing at room temperature to a mixture of olefins unless immediately reacted with trifluoroacetic acid);

f) Preparation of Lithium 2-(6-Fluoro-1-hydroxy-1-indanyl) acetate

A mixture of ethyl 2-(6-fluoro-1-hydroxy-1-indanyl) acetate (2.0 g. 8.4 mmol), 1N lithium hydroxide (8.4 mL) and absolute ethanol (13.0 mL) was stirred for 18 h at room temperature. The mixture was concentrated in vacuo, diluted with H$_2$O and extracted with diethyl ether. The aqueous phase was concentrated in vacuo, diluted with toluene (100 mL) and concentrated in vacuo to give lithium 2-(6-fluoro-1-hydroxy-1-indanyl)acetate as a white solid (1.4 g, 77%);

g) Preparation of (E)-2-(6-Fluoro-1-indanylidene)acetic Acid

Trifluoroacetic acid (1.5 mL) was added to a stirred, chilled (ice-methanol bath) suspension of lithium 2-(6-fluoro-1-hydroxy-1-indanyl)acetate (0.5 g, 2.3 mmol) in dichloromethane (13.5 mL). After 15 min, the mixture was concentrated in vacuo and the resulting white solid was recrystallized from aqueous acetone to give (E)-2-(6-fluoro-1-indanylidene)acetic acid as white crystals (0.32 g, 73%) identical to compound of Example 1i by mixed m.p., (203°–205° C.) and NMR;

h) Preparation of (E)-2-(6-Fluoro-1-indanylidene)acetic Acid

Trifluoroacetic acid (100 mL) was added to a stirred, chilled (ice-methanol bath) solution of 2-(6-Fluoro-1-hydroxy-1-indanyl)acetic acid (37.5 g, 0.18 mol) in dichloromethane (900 mL). After 15 min, the mixture was concentrated in vacuo to give (E)-2-(6-fluoro-1-indanylidene) acetic acid as a yellowish-tan solid (33.0 g, 95%), m.p., 203°–205° C.;

i) Preparation of (E)-2-(6-Fluoro-1-indanylidene)acetyl Chloride

An ice-cold, stirred suspension of (E)-2-(6-fluoro-1-indanylidene) acetic acid (384 mg, 2 mmol) in benzene (10 mL) was treated with oxalyl chloride (761 mg, 6 mmol) and allowed to warm to room temperature during 1.5 h. The resulting yellow solution was concentrated in vacuo to give (E)-2-(6-fluoro-1-indanylidene)acetyl chloride as a pale yellow solid (421 mg, 100%), m.p., 97°–99° C.;

j) Preparation of (E)-2-(6-Fluoro-1-indanylidene)acetamide

A 29.6% aqueous ammonium hydroxide solution (17.6 mL, 134 mmol) was added dropwise to a stirred, chilled (ice bath) solution of (E)-2-(6-fluoro-1-indanylidene)acetyl chloride (14.1 g, 67 mmol) in dichloromethane (165 mL). After an hour, the resulting white precipitate was collected by filtration, dissolved in ethyl acetate (600 mL) and washed with water (3×300 mL). The ethyl acetate layer was dried over sodium sulfate and concentrated in vacuo. The resulting off-white solid was washed with hexane, giving 11.6 g (91%) of (E)-2-(6-fluoro-1-indanylidene)acetamide, m.p., 180°–183° C.;

EXAMPLE 2

Preparation of (E)-2-(6-Fluoro-1-indanylidene) acetamide

A stirred suspension of(E)-2-(6fluoro-1-indanylidene) acetic acid (0.5 g, 2.6 mmol) in dichloromethane (10 mL) at −20° C. was successively treated dropwise with ethyl chloroformate (0.3 g, 2.6 mmol, Aldrich) and triethylamine (0.3 g, 2.6 mmol, Eastman). The mixture was stirred at −20° C. for 2 h. A solution of anhydrous ammonia in dichloromethane (0.8M, 12 mL) was added [Note: When aqueous ammonium hydroxide was used, the mixed anhydride was partially hydrolyzed to the acid.], the mixture was stirred for 16 h at room temperature, and subsequently washed successively with water, sodium bicarbonate solution, water and brine. The dichloromethane layer was dried over sodium sulfate, filtered, and concentrated in vacuo to give 0.18 g of a 6:1 mixture of (E)-2-(6-fluoro-1-indanylidene)acetamide and 2-(5-fluoro-1H-inden-3-yl)acetamide.

EXAMPLE 3

Preparation of (E)-N-Ethyl-2-(6-fluoro-1-indanylidene)acetamide

This compound was prepared in an analogous manner to that of Example 5 with replacement of cyclopropylamine in Example 5 with ethylamine (70 wt % in water). The chromatography solutions that contained (E)-N-Ethyl-2-(6-fluoro-1-indanylidene)acetamide were concentrated by spin evaporation in vacuo. Recrystallization of the residue from dichloromethane-hexanes gave 1.7 g (68%) of (E)-N-ethyl-2-(6-fluoro-1-indanylidene)acetamide, m.p. 125°–127° C.;

EXAMPLE 4

Preparation of (E)-N-Cyclopropyl-2-(6-fluoro-1-indanylidene)acetamide

To an ice-cold stirred solution of (E)-2-(6-Fluoro-1-indanylidene)acetyl Chloride in dichloromethane (50 ml) was added cyclopropylamine (1.65 g, 28.86 mmol) and the reaction was warmed to room temperature overnight. The reaction was evaporated in vacuo to a solid residue. This residue was dissolved in ethyl acetate (300 ml), washed with water (75 ml), and the organic layer was concentrated by spin evaporation in vacuo. The residue was chromatographed on silica gel using ethyl acetate-hexanes (0:1 to 1:1 gradient) as eluent. Fractions containing only the product were combined and concentrated by spin evaporation in vacuo. Recrystallization of the residue from dichloromethane-hexanes gave 1.6 g (76%) of (E)-N-cyclopropyl-2-(6-fluoro-1-indanylidene)acetamide as a white powdery solid, m.p. 124°–127° C.;

(E)-N-Ethyl-2-(6-fluoro-1-indanylidene)-N-methylacetamide was prepared in an analogous manner with replacement of cyclopropylamine with N-ethylmethylamine (3.5 mL, 0.025 mol, Aldrich). The residue was chromatographed on silica gel using ethyl acetate-hexanes (1:5 to 1:2 gradient) as eluent. The chromatography fractions that contained (E)-N-ethyl-2-(6-fluoro-1-indanylidene)-N-methylacetamide were concentrated by spin evaporation in vacuo. Recrystallization of the residue from ethyl acetate-hexanes gave 1.32 g (61%) of (E)-N-ethyl-2-(6-fluoro-1-indanylidene)-N-methylacetamide as a white solid, m.p. 74°–77° C.;

EXAMPLE 5

Preparation of (E)-2-(4,6 Difluoro-1-indanylidene) acetamide a) Preparation of 3-(2,4-Difluorophenyl)propanoic Acid A mixture of 2,4-difluorocinnamic acid (30.0 g, 0.16 mol, Aldrich) and platinum oxide hydrate (0.5 g, EM Scientific) in 95% ethanol (140 mL) was placed on a Parr hydrogenation apparatus. After the appropriate amount of hydrogen was taken up, the catalyst was filtered and the filtrate was concentrated in vacuo to give 29.7 g (98%) of 3-(2,4-difluorophenyl)propanoic acid as a white solid. Recrystallization of 1.0 g from acetonitrile: water mixtures gave 0.61 g of 3-(2,4-difluorophenyl)propanoic acid as a white solid: mp 104°–106° C.; NMR (DMSO-$d_6$); d 12.2 (br, 1H), 6.98–7.40 (m, 3H), 2.81 (t, 2H), 2.51 (t, 2H).

Anal. Calcd. for $C_9H_8F_2O_2$ (mw 186.15): C, 58.06; H, 4.33. 3. Found: C, 57.94; H, 4.36.

b) Preparation of 4,6-Difluoro-1-indanone

To a mixture of 3-(2,4-difluorophenyl) propanoic acid (28.7 g, 0.15 mol) and dimethylformamide (5 drops) at ambient temperature was added dropwise oxalyl chloride (50 mL, Aldrich). The mixture was stirred at ambient temperature for 18 h. The excess oxalyl chloride was removed by distillation in vacuo to give 3-(2,4-difluorophenyl)propionyl chloride. A solution of the 3-(2,4-difluorophenyl)propionyl chloride in dichloromethane (300 mL) was added dropwise to a mixture of aluminum chloride (23.4 g, 0.18 mol, Aldrich) in dichloromethane (300 mL) at ice bath temperature. After the addition was completed, the mixture was refluxed for 3.5 h and allowed to come to ambient temperature over-night. The reaction mixture was poured into ice water (I1500 mL), the two phases were separated and the aqueous phase was extracted with dichloromethane. The combined organic phase was washed successively with 0.1N aqueous sodium hydroxide and saturated sodium chloride solution, dried over sodium sulfate and concentrated in vacuo to give 21.7 g of crude 4,6-difluoro-1-indanone. Chromatography on silica gel with hexanes: dichloromethane (3:1) as eluent gave 10.1 g of a light yellow solid. Recrystallization of 0.5 g from acetone: water mixtures gave 0.2 g of 4,6-difluoro-1-indanone as a white solid: mp 97°–99° C.; NMR (CDCl$_3$): d 7.02–7.27 (m, 2H), 3.12 (t, 2H), 2.76 (m, 2H).

Anal. Calcd. for $C_9H_6F_2O$ (mw 168.14): C, 64.29, H, 3.60. Found: C, 64.18; H, 3.61.

c) Preparation of Ethyl 2-(4,6-Difluoro-1-hydroxy-1-indanyl)acetate

A mixture of 4,6-difluoro-1-indanone (12.6 g, 0.08 mol), ethyl bromoacetate (19.0 g, 0.11 mol, Aldrich), activated zinc powder (7.5 g, 0.11 mol, Aldrich; Org. Syn., Coll. Vol. 6, 290, 1988) and a few crystals of iodine in diethyl ether:toluene (1:1, 300 mL) was heated at 30°–35° C. under a nitrogen atmosphere for 24 h. A few more crystals of iodine were added, the temperature was adjusted to 40°–45° C., and the mixture was kept at that temperature for an additional 24 h. The reaction mixture was filtered and concentrated in vacuo. The residue was treated with a mixture of diethyl ether (450 mL), concentrated ammonium hydroxide (135 mL) and water (135 mL). The aqueous phase was separated and extracted with diethyl ether. The combined organic phase was washed with saturated aqueous sodium chloride solution, dried over sodium sulfate, filtered and concentrated in vacuo to give 22.7 g of crude Ethyl 2-(4,6-difluoro-1- hydroxy-1-indanyl)acetate which was Chromatographed on silica gel with dichloromethane:hexanes (9:1) as eluent gave 12.7 g (66%) of a yellow oil; NMR (CDCl$_3$): d 6.67–6.88 (m, 2H), 4.22 (q, 2H), 3.02 (m, 1H), 2.75 (2 m's, 3H), 2.31 (m, 2H), 1.28 (t, 3H).

Anal. Calcd. for $C_{13}H_{14}F_2O_3$ (mw 256.24): C, 60.93; H, 5.51. Found: C, 60.68; H, 5.50.

d) Preparation of 2-(4,6-difluoro-1-hydroxy-1-indanyl) acetic Acid

A mixture of ethyl 2-(4,6-difluoro-1-hydroxy-1-indanyl) acetate (12.0 g 0.047 mol) and 1.0N sodium hydroxide (48 mL, 0.048 mol, Universal Scientific Supply Co.) in ethanol (75 mL) was stirred for 18 h at ambient temperature. The reaction mixture was concentrated in vacuo, diluted with water and washed with diethyl ether. The aqueous phase was neutralized with 1.0N hydrochloric acid (48 mL, 0.048 mol, Universal Scientific Supply Co.) and extracted with diethyl ether. The diethyl ether extract was dried over sodium sulfate, filtered and concentrated in vacuo to give a quantitative yield of crude 2-(4,6-difluoro-1-hydroxy-1-indanyl) acetic acid. This material was used immediately without further purification.

e) Preparation of (E)-2-(4,6-difluoro-1-indanylidene)acetic Acid

Trifluoroacetic acid (39.9 g, 0.35 mol) was added dropwise to a stirred, chilled (ice-methanol bath) mixture of 2-(4,6-difluoro-1-hydroxy-1-indanyl)acetic acid (11.3 g, 0.05 mol) in dichloromethane (250 mL). After 35 min. the mixture was concentrated in vacuo. Dichloromethane was added to the residue and the mixture was concentrated in vacuo. This procedure was repeated once more to give 6.4 g of crude (E)-2-(4,6- difluoro-1-indanylidene) acetic acid. Recrystallization of 0.9 g from acetone: water mixtures gave 0.15 g of (E)-2-(4,6-difluoro-1-indanylidene) acetic acid as a white solid: mp 238°–239° C.; NMR (DMSO-$d_6$): d12.25 (br, 1H), 7.23–7.65 (m, 2H), 6.46 (t, 1H), 3.20–3.28, 2.97–3.20(2 m's, 4H); steady-state nOe: irradiation at 6.46 d, observed 21.6% nOe at 7.63 d.

Anal. Calcd. for $C_{11}H_8F_2O_2$ (mw 210.17): C, 62.86; H, 3.84. Found: C, 62.76; H, 3.86.

f) Preparation of (E)-2-(4,6-difluoro-1-indanylidene)acetyl Chloride

A suspension of (E)-2-(4,6difluoro-1-indanylidene)acetic Acid (5.49 g, 0.026 mol) in a mixture of dichloromethane: dimethylformamide (50 mL: 5 drops) was treated with oxalyl chloride (6.6 g 0.052 mol, Aldrich) and allowed to stir at ambient temperature for 18 h. The resulting solution was concentrated in vacuo and the residue used without further purification.

g) Preparation of (E)-2-(4,6-difluoro-1-indanylidene) acetamide

A 30% aqueous ammonium hydroxide solution (1.7 mL, 0.026 mol) was added dropwise to a stirred, chilled (ice bath) solution of (E)-2-(4,6-difluoro-1-indanylidene)acetyl chloride (2.97 g, 0.013 mol) in dichloromethane (50 mL). After 4.5 h the mixture was concentrated in vacuo and the residue was partitioned between 5% aqueous sodium bicarbonate solution and ethyl acetate. The ethyl acetate solution was washed with saturated aqueous sodium chloride, dried over sodium sulfate, filtered and concentrated in vacuo Chromatography on silica gel with ethyl acetate: hexanes (7:3)as eluent and trituration of the resulting solid with pentane gave 1.63 g (60%) of (E)-2-(4,6difluoro-1-indanylidene)acetamide as a white solid: mp 178°–180° C.; NMR (DMSO-$d_6$): d 6.94–7.45 (m, 4H), 6.46 (s, 1H), 2.94–3.00, 3.21–3.27 (2 m's, 4H); steady-state nOe: irradiation at 6.46 d, observed 19% nOe at 7.26 d.

Anal. Calcd. for $C_{11}H_9F_2NO$ (mw 209.19): C, 63.15; H, 4.34; N, 6.70. Found: C, 63.07; H, 4.36; N, 6.67.

h) Preparation of (E)-2-(4-chloro-1-indanylidene)acetic Acid

Trifluoroacetic acid (25.1 mL) was added to a stirred, chilled (ice-methanol bath) solution of 2-(4-chloro-1-hydroxy-1-indanyl)acetic acid (10.4 g, 0.05 mol) in dichloromethane (230 mL). After 30 min, the mixture was concentrated in vacuo. Dichloromethane was added to the residue and the mixture was concentrated in vacuo to give 6.5 g (68%) of a white solid. Recrystallization of 0.98 g from acetonitrile: 2-propanol mixtures gave 0.62 g of a white solid: m.p., 233°–234° C.; NMR (DMSO-$d_6$): d12.15 (br, 1H, COOH), 7.30–7.81 (m, 3H, Ar), 6.41 (s, 1H, =CH) 3.00–3.06, 3.19–3.22 (2m's, 4H, 2×$CH_2$), steady-state nOe; irradiation at 6.41 d, observed 19.7% nOe at 7.79.

i) Preparation of (E)-2-(4-chloro-1-indanylidene) acetyl Chloride

A suspension of (E)-2-(4-chloro-1-indanylidene)acetic acid (5.5 g, 0.03 mol) in a mixture of dimethylformamide: dichloromethane (5 drops: 50 mL) was treated with oxalyl chloride (6.6 g, 0.05 mol) and allowed to stir at room temperature for 18 h. The resulting solution was concentrated in vacuo and the residue used without further purification.

j) Preparation of (E)-2-(4-chloro-1-indanylidene)-N-cyclopropylacetamide

An ice cold solution of (E)-2-(4-choro-1-indanylidene) acetyl chloride (2.95 g, 0.013 mol ) in dichloromethane (30 mL) was treated with cyclopropylamine (1.48 g, 0.026 mol, Aldrich) and the mixture was stirred for 4 h. The mixture was concentrated in vacuo and the residue was taken up in a mixture of ethyl acetate and 5% aqueous sodium bicarbonate. The ethyl acetate phase was washed with 5% aqueous sodium bicarbonate, saturated aqueous NaCl and dried ($Na_2SO_4$). Filtration and concentration gave 3.5 g of crude oil product. Chromatography on Silca gel with ethyl acetate: hexanes (1:1) as eluent and trituration of the resulting solid with hexanes gave 2.46 g (76%) of (E)-2-(4-chloro-1-indanylidene)-N-cyclopropylacetamide as an off-white solid: m.p., 140°–142° C.; NMR (DMSO-$d_6$): d 8.16, d, 1H, NH), 7.29–7.51 (m, 3H, Ar), 6.34 (t, 1H, =CH), 2.93–3.07, 3.18–3.31 (2m's, 4H 2X$CH_2$), 2.72 (m, 1H, CH), 0.62–0.72, 0.39–0.47 (2m's, 4H, 2X$CH_2$); steady-state nOe: irradiation at 6.34 d, observed 20.3% nOe at 7.46 d.

Anal. Calcd. for $C_{14}H_{14}ClNO$ (mw 247.72): C, 67.88; H, 5.70; N 5.65. Found: C, 67.86; H, 5.74; N, 5.58.

EXAMPLE 6

Preparation of (E)-N-Cyclopropyl-2-(4,6 difluoro-1-indanylidene)acetamide

An ice cold solution of (E)-2-(4,6-difluoro-1-indanylidene)acetyl chloride (2.97 g, 0.013 mol) in dichloromethane (30 mL) was treated with cyclopropylamine (1.48 g, 0.026 mol, Aldrich) and the mixture was stirred for 4 h. The mixture was concentrated in vacuo and the residue was taken up in a mixture of ethyl acetate and 5% aqueous sodium bicarbonate. The ethyl acetate phase was washed with 5% aqueous sodium bicarbonate, saturated aqueous NaCl and dried ($Na_2SO_4$). Chromatography on silica gel with ethyl acetate: hexanes (1:1) as eluent and trituration of the resulting solid with pentane gave 1.92 g (59%) of (E)-N-cyclopropyl-2-(4,6-difluoro-1-indanylidene) acetamide as a white solid: m.p., 156°–158° C.;

EXAMPLE 7

Preparation of (E)-2-(4-Fluoro-1-indanylidene) acetamide a) Preparation of Ethyl 2-Fluorocinnamate A solution of 2-fluorocinnamic acid (48.4 g, 0.29 mol, Aldrich) and thionyl chloride (5 mL) in ethanol (650 mL) was heated to reflux for 48 h. The mixture was concentrated in vacuo. The residue was taken up in ethyl acetate, washed successively with a 5% aqueous sodium bicarbonate solution, water and brine, and dried ($Na_2SO_4$). Filtration and concentration gave 54.25 g (96%) of crude ethyl 2-fluorocinnamate. This material was used without further purification.

b) Preparation of Ethyl 3-(2-fluorophenyl)propionate

A mixture of ethyl 2-fluorocinnamate (29.25 g, 0.176 mol) and platinum oxide hydrate (0.25, EM Scientific) in 95% ethanol (150 mL) was placed on a Parr hydrogenation apparatus and shaken under 2–4 atm at hydrogen pressure. After the appropriate amount of hydrogen was consumed, the catalyst was removed by filtration, and the filtrate was concentrated in vacuo to give 29.39 g (99%) of crude ethyl 3-(2-fluorophenyl)propionate. This material was used without further purification.

c) Preparation of 3-(2-Fluorophenyl)propionic acid

A mixture of ethyl 3-(2-fluorophenyl)propionate (25.54 g, 0.130 mol) and a 50% aqueous solution of sodium hydroxide (30 mL) in water (130 mL) was refluxed for 2 h. After cooling the mixture was washed with diethyl ether (2×100 mL). The aqueous phase was chilled in an ice bath, and the pH was adjusted to 3 with hydrochloric acid. The white precipitate which formed was collected by filtration, washed repeatedly with water, and dried in a vacuum at 60° C. for 18 h to give 18.66 g (85%) of 3-(2-fluorophenyl)propionic acid as a white solid; m.p., 72°–74° C. This material was used without further purification.

d) Preparation of 4-fluoro-1-indanone

To a mixture of 3-(2-fluorophenyl)propionic acid (18.64 g, 0.111 mol) and dimethylformamide (5 drops) at room temperature was added dropwise oxalyl chloride (60 mL). The mixture was stirred at room temperature until gas evolution had ceased. The excess oxalyl chloride was removed by distillation to give 3-(2-fluorophenyl)propionyl chloride. A solution of the 3-(2-fluorophenyl)propionyl chloride in dichloromethane (230 mL) was added dropwise to a mixture of aluminum chloride (16.25 g, 0.12 mol) in dichloromethane (230 mL), and the mixture was refluxed for 3.5 h. The reaction mixture was poured into ice water (1200 mL), and the two phases were separated. The dichloromethane phase was washed successively with 0.1N aqueous sodium hydroxide (2×100 mL), water (200 mL), and brine (200 mL), dried over sodium sulfate, filtered, and concentrated in vacuo. The residual oil was chromatographed on silica gel eluting with hexane:dichloromethane (9:1) to give 11.0 g of crude 4-fluoro-1-indanone as a yellow solid. Recrystallization from acetone: water mixtures gave 8.02 g (48%) of 4-fluoro-1-indanone as a pale yellow solid: m.p., 71°–72° C.; NM (DMSO-$d_6$): d 7.51 (m, 3H, Ar), 3.13 (t, 2H, $CH_2$), 2.74 (t, 2H, $CH_2$).

Anal. Calcd. for $C_9H_7FO$ (mw 150.152): C, 71.99; H, 4.70. Found: C, 71.86; H, 4.79.

e) Preparation of Ethyl 2-(4-fluoro-1-hydroxy-1-indanyl) acetate

This compound was prepared in an analogous manner to that described in Example 5c for ethyl 2-(4,6-difluoro-1-hydroxy-1-indanyl)acetate substituting 4-fluoro-1-indanone (15.53 g, 0.103 mol) for 4,6-difluoro-1-indanone. Chromatography on silica gel with ethyl acetate:hexanes (19:1) as eluent gave 19.11 g (78%) of ethyl 2-(4-fluoro-1-hydroxy-1-indanyl)acetate which was used without further purification.

f) Preparation of 2-(4-fluoro-1-hydroxy-1-indanyl)acetic Acid

This compound was prepared in a similar manner to that described for 2-(4,6-difluoro-1-hydroxy-1-indanyl)acetic acid in Example 5d by substituting ethyl 2-(4-fluoro-1-hydroxy-1-indanyl)acetate (17.35 g, 0.0728 mol) for ethyl 2-(4,6-difluoro-1-hydroxy-1-indanyl) acetate to give a quantitative yield of crude 2-(4-fluoro-1-hydroxy-1-indanyl) acetic acid. This material was used immediately without further purification.

g) Preparation of (E)-2-(4-fluoro-1-indanylidene)acetic Acid

This compound was prepared in an analogous manner to (E)-2-(4,6-difluoro-1-indanylidene)acetic acid in Example 5e by substituting 2-(4-fluoro-1-hydroxy-1-indanyl)acetic acid (14.6 g, 0.069 mol) for 2-(4,6-fluoro-1-hydroxy-1-indanyl)acetic acid to give crude (E)-2-(4-fluoro-1-indanylidene)acetic acid. Recrystallization from acetonitrile: 2-propanol mixtures gave 6.85 g (52%) of (E)-2-(4-fluoro-1-indanylidene)acetic acid as a white solid; m.p., 249°–251° C.;

h) Preparation of (E)-2-(4-fluoro-1-indanylidene)acetyl Chloride

This compound was prepared in a similar manner to (E)-2-(4,6difluoro-1-indanylidene)acetyl chloride in Example 5f by substituting (E)-2-(4-fluoro-1-indanylidene) acetic acid (5.77 g, 0.03 mol) for (E)-2-(4,6-difluoro-1-indanylidene)acetic acid. The resulting solution was concentrated in vacuo, and the residue was used without further purification.

i) Preparation of (E)-2-(4-fluoro-1-indanylidene)acetamide

An ice cold solution of(E)-2-(4-fluoro-1-indanylidene) acetyl chloride (2.11 g, 0.01 mol) in dichloromethane (65 mL) was treated with a 30% aqueous solution of ammonium hydroxide (2.63 ml, 0.02 mol), and the mixture was stirred for 18 h. Hexane was added to the mixture, and the solids were collected by filtration to give 1.63 g of crude product. Recrystallization from acetonitrile: water mixtures gave 1.11 g (58%) of (E)-2-(4-fluoro-1-indanylidene)-acetamide as a white solid; m.p., 198°–200° C.;

EXAMPLE 8

Preparation of (E)-2-N-cyclopropyl-(4-fluoro-1-indanylidene)acetamide

An ice cold solution of (E)-2-(4-fluoro-1-indanylidene) acetyl chloride (2.11 g, 0.010 mol) in dichloromethane (65 mL) was treated with cyclopropylamine (1.39 mL, 0.02 mol), and the mixture was stirred for 18 h. Hexane was added to the mixture, and the solids were collected by filtration and washed successively with water and hexane to give 1.22 g of crude product. Recrystallization from acetonitrile: water mixtures gave 0.83 g (36%) of (E)-2-N-cyclopropyl-(4-fluoro-1-indanylidene)acetamide as a white solid; m.p., 121°–122° C.;

EXAMPLE 9

Preparation of (E)-2-(5-fluoro-1-indanylidene) acetamide a) Preparation of Ethyl 2-(5-fluoro-1-hydroxy-1-indanyl) acetate This compound was prepared in an analogous manner to that described in Example 5c for ethyl 2-(4,6-difluoro-1-hydroxy-1-indanyl) acetate substituting 5-fluoro-1-indanone (14.77 g, 0.098 mol, Fairfield) for 4,6-difluoro-1-indanone. Chromatography on silica gel with ethyl acetate: hexanes (9:1) as eluent gave 19.56 g (83%) of analytically pure ethyl 2-(5-fluoro-1-hydroxy-1-indanyl)acetate as a pale yellow oil; NMR (CDCl$_3$): d 6.88–7.30 (m, 3H, Ar), 5.30 (s, 1H, OH), 4.20 (q, 2H, $CH_2CH_3$), 2.66–3.08 (m, 4H, 2$CH_2$), 2.30 (t, 2H, $CH_2$Ar), 1.28 (t, 3H, $CH_3$).

Anal. Calcd. for $C_{13}H_{15}FO_3$ (mw 238.25): C, 65.54; H, 6.35. Found: C, 65.39; H, 6.33.

b) Preparation of 2-(5-fluoro-1-hydroxy-1-indanyl)acetic Acid

This compound was prepared in a similar manner to that described for 2-(4,6-difluoro-1-hydroxy-1-indanyl)acetic acid in Example 5d by substituting ethyl 2-(5-fluoro-1-hydroxy-1-indanyl) acetate (19.55 g, 0.082 mol) for ethyl 2-(4,6-difluoro-1-hydroxy-1-indanyl) acetate to give 14.70 g (84%) of crude 2-(5-fluoro-1-hydroxy-1-indanyl) acetic acid as a white solid. This material was used immediately without further purification.

c) Preparation of (E)-2-(5-Fluoro-1-indanylidene)acetic Acid

This compound was prepared in an analogous manner to (E)-2-(4,6difluoro-1-indanylidene)acetic acid in Example 5e by substituting 2-(5-fluoro-1-hydroxy-1-indanyl)acetic acid (14.70 g, 0.069 mol) for 2-(4,6-difluoro-1-hydroxy-1-indanyl)acetic acid. Recrystallization from acetonitrile: 2-propanol mixtures gave 9.05 g (68%) of (E)-2-(5-fluoro-1-indanylidene)acetic acid as a white solid: m.p., 240°–242° C.;

d) Preparation of (E2-(5-fluoro-1-indanylidene)acetyl Chloride

This compound was prepared in a similar manner to (E)-2-(4,6-difluoro-1-indanylidene)acetyl chloride in Example 5f by substituting (E)-2-(5-fluoro-I-indanylidene) acetic acid (5.77 g, 0.03 mol) for (E)-2-(4,6-difluoro-1-indanylidene)acetic acid. The resulting solution was concentrated in vacuo, and the residue was used without further purification.

e) Preparation of (E)-2-(5-fluoro-1-indanylidene)acetamide

This compound was prepared in a similar manner to that described for (E)-2-(6-fluoro-1-indanylidene)acetamide Example 1k by substituting (E)-2-(5-fluoro-1-indanylidene) acetyl chloride (3.16 g, 0.015 mol) for (E)-2-(6-fluoro-1-indanylidene)acetyl chloride. Recrystallization from acetonitrile: water mixtures gave 1.28 g (44%) of (E)-2-(5-fluoro-1-indanylidene)acetamide as a white solid; m.p., 191°–193° C.;

EXAMPLE 10

Preparation of (E)-N-Cyclopropyl-2-(5-fluoro-1-indanylidene)acetamide

A solution of (E)-2-(5-fluoro-1-indanylidene)acetic acid (0.97 g, 0.005 mol), 1-hydroxybenzotriazole (0.68 g, 0.005 mol, Fluka), cyclopropylamine (0.35 mL, 0.005 mol, Aldrich) and 1-(3-dimethylaminopropyl)-3-ethylcarbodiimide hydrochloride (0.96 g, 0.005 mol, Sigma), which was added last, in dimethylformamide (15 mL) was stirred at room temperature for 18 h, and the solution was concentrated in vacuo. The residue was dissolved in ethyl acetate, washed successively with a 5% aqueous solution of citric acid (3×50 mL), a saturated aqueous sodium bicarbonate solution (2×50 mL) and brine, and dried over sodium sulfate. The solution was concentrated in vacuo to give crude (E)-N-cyclopropyl-2-(5-fluoro-1-indanylidene)acetamide. Chromatography on Silica gel eluting with hexane: ethyl acetate (1:1) gave 0.52 g (44%) of (E)-N-cyclopropyl-2-(5-fluoro-1-indanylidene)acetamide as a white solid: m.p., 137°–138° C.;

EXAMPLE 11

Alternative Preparation of (E)-2-(6Fluoro-1-indanylidene)acetamide

To an ice-cold stirred suspension of NaH (60% dispersion in mineral oil, 12.41 g, 60.25 mmoles, Aldrich) in tetrahydrofuran (30 ml) with 15-crown-5 (3.96 g, 17.98 mmoles, Aldrich) was added under $N_2$, diethyl carbamoylmethylphosphonate (11.7 g, 59.97 mmoles, K&K-ICN) and 6-fluoro-1-indanone (9.0 g, 59.96 mmol) respectively in tetrahydrofuran (80 ml ). The mixture was allowed to warm to room temperature overnight. The mixture was poured into 200 ice-cold water and extracted with three 600 ml portions of diethyl ether. One organic phase was washed successively with 200 ml portions of aqueous sodium bisulfite (10%) and a saturated sodium chloride solution. The organic phase was dried over potassium carbonate, filtered, spin evaporated in vacuo and coevaporated with 200 ml dichloromethane to yield a tacky solid residue. The residue was chromatographed on Silica Gel 60 using ethyl acetate:hexane (2:1). Fractions containing (E)-2-(6-fluoro-1-indanylidene) acetamide were combined and spin evaporated in vacuo to give 2.38 g of a yellow solid. Dilution of a dichloromethane solution of the crude material with hexane gave 2.16 g (18.8%) of (E)-2-(6-fluoro-1-indanylidene)acetamide, m.p., 178°–182° C.; NMR (DMSO-$d_6$); d 7.4–7.1 (m, 4H, Ar and NH), 6.88 (br s, 1H, NH), 6.37 (t, 1H, J=2.54 Hz, =CH), 3.22–3.14 (m, 2H $CH_2$), 2.95–2.89 (m, 2H, $CH_2$); steady-state nOe: irradiation at d 6.37, significant observed nOe at d 7.33–7.28.

Anal. Calcd for $C_{11}H_{10}FNO$: C, 69.10;H, 5.27; N, 7.33 Found: C, 69.01; H, 5.29; N, 7.28.

EXAMPLE 12

Preparation of (E)-N-Cyclopropyl-2-(5-fluoro-1,2,3,4-tetrahydro-1-naphthylidene)acetamide a) Preparation of 2-(2-Fluorophenyl)ethylbromide To a mixture of aqueous hydrobromic acid (48%, 360 mL) and concentrated sulfuric acid (103.6 mL) at room temperature was added dropwise 2-(2-fluorophenyl)ethanol (250 g, 1.78 mol, Aldrich). The reaction mixture was refluxed for 7 h, poured onto 600 ml of ice and the mixture was extracted with diethyl ether. The diethyl ether extracts were washed successively with saturated sodium carbonate and brine. The organic phase was dried ($MgSO_4$) and concentrated in vacuo to give 359.9 g (99%) of 2-(2-fluorophenyl)-ethylbromide as a brown oil. This product was used without further purification. NMR ($CDCl_3$: d 7.6–6.9 (m. 4H, ArH), 3.6 (t, 2H $CH_2$), 3.2 (t, 2H, $CH_2$).

b) Preparation of Diethyl 2-(2-(2-fluorophenyl) ethylmalonate

To absolute ethanol (1.5 L) at room temperature under a nitrogen atmosphere was added sodium metal (61.1 g, 2.66 mol) in small pieces over several hours. After stirring for 24 h at room temperature, the mixture was warmed to 40° C., and dimethyl malonate (525.4 g, 3.28 mol) was added dropwise followed by 2-(2-fluorophenyl)ethylbromide (359.9 g, 1.77 mol). The mixture was refluxed for 8 h. The crude material was purified by vacuum distillation at 85°–130° C. and 0.60 mm Hg to give 312.6 g (62%) of diethyl 2-(2-(2-fluorophenyl)ethyl)malonate as a clear oil. NMR ($CDCL_3$): d 7.6–7.0 (m, 4H, ArH), 4.2 (q, 4H, 2X $CH_2$) 3.4 (t, 1H, CH), 2.6 (q, 2H, $CH_2$), 2.2 (t, 2H, $CH_2$), 1.2 (t, 6H, 2X $CH_3$).

c) Preparation of 2-[2-(2-Fluorophenyl)ethyl]malonic acid

A mixture of diethyl 2-(2-(2-fluorophenyl)ethyl)malonate (381.8 g, 1.35 mol) and potassium hydroxide (227.3 g, 4.1 mol) and potassium hydroxide (227.3 g, 4.1 mol) in ethanol (500 mL) and water (500 mL) was refluxed for 24 h. The reaction mixture was placed in an ice bath and hydrochloric acid (6N, 442 mL) was added. The ethanol was removed in vacuo and the aqueous residue was extracted with diethyl ether. The extracts were dried ($MgSO_4$) and concentrated in vacuo to give 309.3 g (100%) of 2-(2-(2-fluorophenyl)ethyl) malonic acid as an off-white solid. This product was used without further purification. NMR (DMSO-$d_6$): d 6.8–6.2 (m, 4H, ArH), 2.4 (t, 1H, CH), 1.9 (q, 2H, $CH_2$), 1.3 (t, 2H, $CH_2$). IR ($KB_r$) 1691 $CM^{-1}$.

d) Preparation of 4-(2-Fluorophenyl)butyric acid

The 2-(2-(2-fluorophenyl)ethyl)malonic acid (147 g, 0.65 mol) was heated in an oil bath at 170° C. for 2.5 h. On cooling, 4-(2-fluorophenyl)butyric acid (117.3 g, 99%) crystallized as a tan solid. This product was used without further purification. NMR (CDCl$_3$): d 7.6–7.0 (m, 4H, ArH), 3.0–1.8 (m, 6H, 3X CH$_2$). IR (neat) 1709 cm$^{-1}$.

e) Preparation of 5-Fluorotetralone

A mixture of 4-(2-fluorophenyl)butyric acid (100 g, 0.55 mol) and thionyl chloride (418.8 g, 3.51 mol) was refluxed for 3 h. The excess thionyl chloride was removed in vacuo to give 110.1 g (100%) of 4-(2-fluorophenyl)butyryl chloride.

To the 4-(2-fluorophenyl)butyryl chloride in carbon disulfide (1.0 L) at -78° C. was added aluminum chloride (93.2 g, 0.7 mol) portionwise over a 30 min period. The mixture was warmed to room temperature for 30 min, then refluxed for 2 h. The reaction mixture was poured into a mixture of ice (500 mL) and HCl (6N, 500 mL). The carbon disulfide layer was separated, washed with saturated sodium bicarbonate and extracted with ethyl acetate. The aqueous phase was extracted with ethyl acetate. The combined extracts were dried (MgSO$_4$) and concentrated in vacuo to give 84.2 g (93%) of 5-fluorotetralone as a tan solid. NMR (CDCl$_3$): d 7.7 (m, 1H, ArH), 7.1 (m, 2H, ArH), 2.9 (t, 2H, CH$_2$), 2.6 (t, 2H, CH$_2$), 2.1 (q, 2H, CH$_2$).

f) Preparation of (E)-N-Cyclopropyl-2-(5-fluoro-1,2,3,4-tetrahydro-1-naphthylidene)acetamide To a stirred suspension of NaH (60% dispersion in mineral oil, Aldrich) in dimethyl sulfoxide at room temperature under N$_2$ was added diethyl (cyclopropyl carbamoylmethyl) phosphonate (21.5 g, 0.09 mol). The reaction was slightly exothermic. To the resulting solution was added 5-fluoro-1-tetralone (13.7 g, 0.08 mol) in dimethyl sulfoxide. The reaction was stirred overnight at room temperature. The reaction was poured into ice-cold water (800 ml) and extracted with four 500 ml portions dichloromethane. The organic phase was washed with eight 500 ml portions of water, filtered and spin evaporated in vacuo.

Chromatography on Silica gel using 35% to 50% ethyl acetate:hexanes as eluent followed by trituration of the resulting solid with pentane at room temperature gave 5.07 g (25%) of (E)-N-cyclopropyl-2-(5-fluoro-1,2,3,4-tetrahydro-1-naphthylidene)acetamide, m.p., 148°–149° C.;

EXAMPLE 13

Preparation of (E)-N-Cyclopropyl-2-(7-fluoro-1,2,3,4-tetrahydro-1-naphthylidene)acetamide a) Preparation of 3-(4-fluorobenzoyl)propionic acid A mixture of fluorobenzene (104.4 g, 1.09 mol, Aldrich) and succinic anhydride (93.5 g, 0.93 mol) in 1,2-dichlorobenzene (530 mL) was heated to 50° C. Aluminum chloride (245 g, 1.84 mol) was added portionwise keeping the temperature below 60° C. After 4 h at 60° C. followed by 5 h at 80° C., the reaction mixture was poured into a mixture of concentrated HCl (200 mL) and ice water (2 L). The organic layer was separated and the aqueous phase was extracted with dichloromethane. The combined organic phase was dried and concentrated in vacuo. The residue was poured into hexane (2 L) and the resulting solid was filtered and washed with pentane to give 164.1 g (89%) of 3-(4-fluorobenzoyl) propionic acid as a white solid. m.p., 102°–104.5° C. (lit J. Org. Chem. 26, 2667, 1961; m.p., 102.5°–103.5° C.);

b) Preparation of 4-(4-fluorophenyl)butyric acid

A mixture of 3-(4-fluorobenzoyl)propanoic acid (42.3 g, 0.22 mol) and 10% Palladium on carbon (3 g) in acetic acid (250 mL) was hydrogenated at 50 psi and 25° C. for 6 h. The mixture was filtered and concentrated in vacuo. The residue was distilled at 0.02 mm Hg and the product crystallized to give 4-(4-fluorophenyl)butyric acid as a white solid (97%). m.p., 44°–46.2° C. (lit. J. Am. Chem. Soc. 89, 386, 1967; m.p., 45.5°–46.5° C.).

c) Preparation of 7-Fluoro-1-tetralone

A mixture of 4-(4-fluorophenyl)butyric acid (68.2 g, 0.37 mol) and thionyl chloride (155 g, 1.3 mol) was refluxed for 1.25 h. The mixture was concentrated in vacuo to give 75.3 g (100%) of 4-(4-fluorophenyl)butyryl chloride)

To a mixture of aluminum chloride (66 g, 0.50 mol) in carbon disulfide (600 mL) was added dropwise a solution of 4-(4-fluorophenyl)butyryl chloride (75.3 g, 0.37 mole) in carbon disulfide (260 mL) keeping the internal temperature below 10° C. After refluxing for 0.5 h, the reaction mixture was poured into a mixture of concentrated HCl (50 mL) and ice water (800 mL). The mixture was filtered and extracted with diethyl ether. The diethyl ether extracts were dried and concentrated it7 vacuo to give crude 7-fluoro-1-tetralone. Vacuum distillation gave pure 7-fluoro-1-tetralone b.p., 83° C. at 0.3 mm Hg which solidified to a white solid (94%). m.p., 62°–64° C. (lit, J. Am. Chem. Soc., 89, 386, 1967, m.p., 63.5°–65.0° C.);

d) Preparation of (E)-N-Cyclopropyl-2-(7-fluoro-1,2,3,4-tetrahydro-1-naphthylidene)acetamide This compound was prepared in an analogous manner to Example 12f with the replacement of 5-fluoro1-tetralone and diethyl (cyclopropylcarbamoyl)methyl phosphonate with 7-fluoro-1-tetralone (7.76 g, 0.05 mol) and diethyl(cyclo propylcarbamoyl)methylphosphonate (11.1 g, 0.05 mol). Chromatography on Silica gel using ethyl acetate:hexanes (1:2) as eluent gave 4.38 g (37%) of (E)-N-Cyclopropyl-2-(7-fluoro-1,2,3,4-tetrahydro-1-naphthylidene) acetamide, m.p., 122.8°–123.3° C.; NMR (DMSO-d$_6$): d 8.00 (d, J=4.0 Hz,1H), 7.32 (dd, J=11.2 Hz,1H), 7.04–7.23 (m, 2H), 6.33 (s, 1H), 3.06 (m,2H), 2.69 (m, 3H), 1.70 (m, 2H), 0.66 (m, 2H), 0.40 (m, 2H); steady-state nOe: irradiation at 6.39 d, observed significant nOe at 7.32 d.

Anal. Calcd. for C$_{15}$H$_{16}$FNO (mw 245.30): C, 73.45; H, 6.57; N, 5.71. Found: C, 73.38; H, 6.64; N, 5.67.

EXAMPLE 14

Preparation of (E)-2-(7-Fluoro-1,2,3,4-tetrahydro-1-naphthylidene)-N,N-dimethylacetamide a) Preparation of Ethyl 2-(7-Fluoro-1,2,3,4-tetrahydro-1-hydroxy-1-naphthyl)acetate Ethyl acetate (5.4 g, 61 mmol) was added dropwise to a stirred, chilled (dry ice-acetone bath) solution of 1M lithium bis(trimethylsilyl)amide in tetrahydrofuran (61 mL, 0.061 mol, Aldrich) under nitrogen. After 15 min, a solution of 7-fluoro-1-tetralone (10.0 g, 61 mmol) in tetrahydrofuran (25 mL) was added dropwise and the resulting mixture was stirred for 1 h (dry ice-acetone bath). A 1N solution of hydrochloric acid (61 mL) was added and the mixture was allowed to warm to room temperature. The organic phase was separated, dried over anhydrous sodium sulfate, filtered and concentrated to a pale yellow oil (15.0 g, 100%). An analytical sample was obtained by chromatographing a 1.5 g portion on Silica Gel 60 using dichloromethane-hexanes (1:1) as eluent. The fractions containing only ethyl 2-(7-fluoro-1,2,3,4-tetrahydro-1-hydroxy-1-naphthyl)acetate were combined and concentrated iii vacuo to give 1.2 g (80%) of a colorless oil; NMR (DMSO-d$_6$): d 6.93–7.31 (m, 3H, Ar), 5.28 (s, 1H, OH), 3.98 (m, 2H, CH$_2$OOC), 2.60–2.87 (m, 4H, CH$_2$CO, CH$_2$), 2.12–2.28 (m, 1H, CH), 1.78–1.86 (m, 3H, CH, CH$_2$), 1.09 (t, 3H, CH$_3$).

b) Preparation of Ethyl 2-(7-Fluoro-1,2,3,4-tetrahydro-1-naphthyl)acetate

Trifluoroacetic acid (20 mL) was added to a stirred, chilled (ice-methanol bath) solution of crude ethyl 2-(7-fluoro-1,2,3,4-tetrahydro-1-hydroxy-1-naphthyl)acetate (10.0 g, 35.8 mmol) in dichloromethane (180 mL). After 4 h, the mixture was concentrated in vacuo to a clear oil (8.3 g, 100%); NMR (DMSO-$d_6$): d 6.94–7.65 (m, 3H, Ar), 6.45 (br s, 0.2 H, =CH/E), 6.10 (t, 0.8H, =CH/endo), 4.08 (m, 2H, CH$_2$OOC), 3.67, 3.51 (s's, 2.2H, H$_2$O, CH$_2$/endo), 3.08, 2.70, 2.25, 1.77 (m's, 4.4H, 5×CH$_2$), 1.26 (t, 0.6H, CH$_3$/E), 1.17 (t, 2.4H, CH$_3$/endo).

A portion of the above mixture of E and endo esters (2.3 g, 10 mmol), sodium hypophosphite hydrate (1.8 g, 20 mmol, Aldrich) and 10% palladium on carbon (0.2 g) in 75% aq ethanol (20 mL) was heated to reflux for 2 h. The mixture was filtered through celite and the filtrate was concentrated in vacuo. The residue in dichloromethane was washed successively with water (100 mL) and brine (50 mL), dried over anhydrous sodium sulfate, filtered, concentrated in vacuo and chromatographed on Silica Gel 60 using ethyl acetate-hexane (3:97) as eluent. The fractions containing only ethyl 2-(?-fluoro-1,2,3,4-tetrahydro-1-naphthyl)acetate were combined and concentrated in vacuo to give 1.9 g (78%) of a pale yellow oil; NMR (DMSO-$d_6$): d 6.89–7.14 (m, 3H, Ar), 4.11 (q, 2H, CH$_2$OOC), 3.15–3.27 (m, 1H, CH), 2.44–2.82 (m, 4H, 2×CH$_2$), 1.52–1.90 (m, 4H, 2×CH$_2$), 1.20 (t, 3H, CH$_3$).

c) Preparation of Ethyl 2-Bromo-2-(7-fluoro-1,2,3,4-tetrahydro-1-naphthyl)acetate To a stirred, chilled (dry ice-acetone bath) solution of diisopropylamine (0.3 mL, 1.9 mmol, Aldrich) in tetrahydrofuran (3 mL) under nitrogen was successively added 2.5N n-butyl lithium in hexane (0.8 mL, Aldrich), chlorotrimethylsilane (0.2 mL, 1.8 mmol, Aldrich) and ethyl 2-(7-fluoro-1,2,3,4-tetrahydro-1-naphthyl)acetate (236 mg, 1.0 mmol). The resulting clear solution was stirred for 1 h, treated with N-bromosuccinimide (180 mg, 1.0 mmol, Aldrich) and stirred for an additional 0.5 h before the dry ice-acetone bath was removed. The reddish cloudy solution was stirred for 2 h at room temperature, treated with dilute aq hydrochloric acid (4 meq) and extracted with diethyl ether (30 mL). The ether layer was dried over anhydrous sodium sulfate, filtered, concentrated in vacuo and chromatographed on Silica Gel 60 using dichloromethane-hexane (1:9) as eluent. Fractions containing only ethyl 2-bromo-2-(7-fluoro-1,2,3,4-tetrahydro-1-naphthyl)acetate as a 1:4 isomeric mixture were combined and concentrated in vacuo to a clear oil (171mg, 54%); NMR (DMSO-$d_6$): d 7.00–7.18 (m, 3H, Ar), 5.20 (d, J=6.2 Hz, 0.8H, BrCHCO), 5.17 (d, J=6.2 Hz, 0.2H, BrCHCO), 4.19 (q, 1.6H, CH$_2$OOC), 4.14 (q, 0.4H, CH$_2$OOC), 3.49 (m, 1H, ArCH), 2.69 (m, 2H, ArCH$_2$), 1.81–1.97 (m, 3H, CH, CH$_2$), 1.61–1.67 (m, 1H, CH), 1.21 (t, 2.4H, CH$_3$), 1.07 (t, 0.6H, CH$_3$).

d) Preparation of (E)-2-(7-Fluoro-1,2,3,4-tetrahydro-1-naphthylidene)acetic Acid A mixture of ethyl 2-bromo-2-(7-fluoro-1,2,3,4-tetrahydro-1-naphthyl)acetate (2.2 g, 7.0 mmol), 1N potassium tert-butoxide in tetrahydrofuran (14 mL, Aldrich) and tert-butanol (140 mL) was stirred for 5 h at room temperature. The resulting suspension was concentrated in vacuo, diluted with water (200 mL) and washed with diethyl ether. The aqueous layer was acidified by adding 1N hydrochloric acid (14 mL) and extracted with diethyl ether. The ether extract was dried over anhydrous sodium sulfate, filtered, concentrated in vacuo and chromatographed on Silica Gel 60 using ethyl acetate-hexane (1:1) as eluent. The fractions containing only (E)-2-(7-fluoro-1,2,3,4-tetrahydro-1-naphthylidene)acetic acid were combined and concentrated in vacuo to give a white solid (0.8 g, 55%); NMR (DMSO-$d_6$): d 12.22 (br s, 1H, COOH), 7.57 (d of d, $J_m$=2.6 Hz, $J_o$=11.0 Hz, 1H, Ar), 7.12–7.28 (m, 2H, Ar). 6.36 (s, 1H, =CH, E), 3.04 (t, 2H, ArCH$_2$), 2.74 (t, 2H, CH$_2$), 1.74 (m, 2H, CH$_2$); steady-state nOe: irradiation at 6.36, observed 25% nOe at 7.57.

e) Preparation of (E)-2-(7-fluoro-1,2,3,4-tetrahydro-1-naphthylidene)acetyl chloride Oxalyl chloride (3 ml, 0.034 mol, Aldrich) was added to a suspension of (E)-2-(7-fluoro-1,2,3,4-tetrahydro-1-naphthylidene)acetic acid (2.03 g, 0.01 mol) in toluene (35 ml) at 0° C. while protected from moisture by a nitrogen atmosphere. The stirring mixture was allowed to warm to 25° C. and was stirred for 1.5 h. Concentration in vacuo gave (E)-2-(7-fluoro-1,2,3,4-tetrahydro-1-naphthylidene)acetyl chloride which was dissolved in dichloromethane and used without purification.

f) Preparation of (E)-2-(7-fluoro-1,2,3,4-tetrahydro-1-naphthylidene)-N,N-dimethylacetamide Dimethylamine (3 ml, 0.045 mol, Kodak) was added to a chilled (ice bath) solution of (E)-2-(7-fluoro-1,2,3,4-tetrahydro-1-naphthylidene)acetyl chloride (2.3 g, 0.010 mol) in dichloromethane (35 ml). The reaction was warmed to 25° C. and stirred for 1.5 h. The volatiles were removed by spin evaporation in vacuo to give a beige residue. This residue was dissolved in ethyl acetate (200 ml), washed with deionized water (50 ml), and the organic layer was concentrated by spin evaporation in vacuo. The residue was chromatographed on Silica Gel 60 using a step gradient from ethyl acetate-hexanes/1:5 to ethyl acetate. Fractions containing (E)-2-(7-fluoro-1,2,3,4-tetrahydro-1-naphthylidene)-N,N-dimethylacetamide were combined and concentrated by spin evaporation in vacuo to a white solid. Recrystallization from dichloromethane-hexanes gave 1.62 g (70%) of (E)-2-(7-fluoro-1,2,3,4-tetrahydro-1-naphthylidene)-N,N-dimethylacetamide as a white crystalline solid; m.p., 66°–70° C.

Anal.Calcd. for $C_{14}H_{16}FNO$ (mw 233.278); C, 72.08; H,691; N,6.00. Found: C,71.97; H,6.94; N,5.95.

EXAMPLE 15

Preparation of (E)-2-(6-Fluoro-3,3-dimethyl-1-indanylidene)acetamide a) Preparation of Diethyl Isopropylidenemalonate Diethyl isopropylidenemalonate was prepared according to the procedure of E. L. Eliel, R. O. Hutchins, and Sr. M. Knoeber, Organic Synthesis Coll. Vol. VI, 442, 1988, with following modifications. A mixture of acetone (54 g, 0.93 mol, Mallinckrodt), diethyl malonate (100 g, 0.62 mol, Aldrich), acetic anhydride (80 g, 0.78 mol, Mallinckrodt), and zinc chloride (12.5 g, 0.78 mol, Aldrich) was refluxed (90° C. oil bath) for 18 h while protected from moisture. The reaction solution was diluted with dichloromethane (500 ml) and washed with cold water (3×50 ml). The aqueous washes were combined and extracted with dichloromethane. All dichloromethane layers were combined and concentrated by spin evaporation in vacuo. The residual oil was distilled under vacuum and the fractions boiling at 102°–138° C. at 12 Torr were combined with the pot residue and heated for 6 h with a 200° C. oil bath. The dark oil was redistilled to give 40.1 g (32%) of diethyl isopropylidenemalonate as a clear oil: b.p., 110°–115° C./12 mmHg;

b) Preparation of Diethyl 2-(2-(4-Fluorophenyl)-2-methylethyl)malonate

A mixture of 4-fluorophenylmagnesium bromide (82 ml of a 2N solution in ethyl ether, 0.164 mol, Aldrich) and copper(I) iodide (0.310 mg, 1.63 mmol, Aldrich) was stirred for 15 min at −10° C. while blanketed with a nitrogen atmosphere. To this mixture was added a solution of diethyl isopropylidenemalonate (29.6 g, 0.148 mol) in anhydrous diethyl ether (250 ml) in a thin stream with rapid stirring. The resulting solution was stirred at −10° C. for 2 h, at 25° C. for 30 min and then poured with rapid stirring into 0.5 kg of crushed ice containing 30 ml of 12N hydrochloric acid. The layers were separated and the aqueous layer was extracted with ethyl ether (3×400 ml). All ether layers were combined and washed with deionized water (2×25 ml), saturated aqueous sodium bicarbonate (25 ml), and deionized water (25 ml). The etheral layer was concentrated by spin evaporation in vacuo and the residue was distilled to give 25.9 g (59%) of diethyl 2-(2-(4-fluorophenyl)-2-methylethyl)malonate as a clear oil (b.p., 140°–145° C./0.01 mmHg);

c) Preparation of 3-(4-Fluorophenyl)-3-methylbutyric Acid

A solution of diethyl 2-(2-(4-fluorophenyl)-2-methylethyl)malonate (41 g, 0.138 mol) and potassium hydroxide 85% (18.25 g, 0.277 mol, Mallinkrodt) in 250 ml of deionized water was vigorously refluxed for 4 hours with an 150° C. oil bath. After cooling with an ice bath, the solution was neutralized with 18N sulfuric acid (23 ml, 0.414 mol, Mallinkrodt), and extracted with dichloromethane (4×250 ml). The dichloromethane extracts were combined, washed with water, and concentrated by spin evaporation in vacuo. The residue was slurried with water and the crystalline product was collected by filtration to give 24.3 g (90%) of 3-(4-fluorophenyl)-3-methylbutyric acid, m.p., 45°–57° C.;

d) Preparation of 3-(4-Fluorophenyl)-3-methylbutyryl Chloride

Oxalyl chloride (46.5 g, 0.367 mol, Aldrich) was added to a solution of 3-(4-fluorophenyl)-3-methylbutyric acid (24 g, 0.122 mol) at −10° C. while protected from moisture by a nitrogen atmosphere. The stirring mixture was allowed to warm to 25° C. and was stirred for 2 h. Fractional distillation gave 26.6 g (76%) of 3-(4-fluorophenyl)-3-methylbutyryl chloride as a clear oil, b.p., 132°–138° C.;

e) Preparation of 6-Fluoro-3,3-dimethyl-1-indanone

A solution of 3-(4-fluorophenyl)-3-methylbutyryl chloride (19.0 g, 0.0815 mol) in dichloromethane (100 ml) was added dropwise over 2.5 h to a stirring mixture of aluminum chloride (13.57 g, 0.102 mol, Aldrich) in dichloromethane (200 ml) while protected from moisture by a nitrogen atmosphere. After stirring 18 h at 25° C., the reaction solution was poured over ice (400 g) and the resulting solution was extracted with dichloromethane (2×200 ml). The dichloromethane layers were combined, washed with deionized water (50 ml), and concentrated by spin evaporation in vacuo. The residue was dissolved in ethyl acetate and washed through a pad of silica gel. The pad was washed with additional ethyl acetate. Removal of the volatiles from the combined washes by spin evaporation in vacuo gave 15.2 g (99%) of 6-fluoro-3,3-dimethyl-1-indanone as a light yellow oil which crystallized on standing, m.p., 57°–62° C.;

f) Preparation of Ethyl 2-(6-Fluoro-1-hydroxy-3,3-dimethyl-1-indanyl)acetate

This compound was prepared in a similar manner to ethyl 2-(6-fluoro-1-hydroxy-1-indanyl)acetate in Example 1d by substituting 6-fluoro-3,3-dimethyl-1-indanone for 6-fluoro-1-indanone and preparing the activated zinc by heating zinc dust (Aldrich) with iodine (Aldrich) without solvent. Removal of the volatiles from the workup solution by spin evaporation in vacuo gave 16.2 g (82%) of ethyl 2-(6-fluoro-1-hydroxy-3,3-dimethyl-1-indanyl)acetate as a light yellow oil;

g) Preparation of (E)-2-(6-Fluoro-3,3-dimethyl-1-indanylidene)acetic Acid

A solution of ethyl 2-(6-fluoro-1-hydroxy-3,3-dimethyl-1-indanyl)acetate (16 g, 0.0601 mol) in 1N sodium hydroxide (60.1 ml, 0.0601 mol) and ethanol (60 ml) was stirred for 20 h. The solution was concentrated to a small volume by spin evaporation in vacuo, diluted with deionized water (100 ml), and acidified to pH 3 with 1N hydrochloric acid This biphasic solution was extracted with dichloromethane (2×100 ml). The extracts were combined, washed with deionized water (20 ml), dried with magnesium sulfate (Mallinckrodt), and concentrated by spin evaporation in vacuo. The residue was dissolved in dichloromethane (30 ml), cooled to 0° C., and diluted with 400 ml of a cold (0° C.) solution of trifluoroacetic acid (45 g, Aldrich) in dichloromethane (400 ml). After 15 min. the solution was concentrated by spin evaporation in vacuo and the residue was crystallized by adding hexanes to give 9.23 g (70%) of (E)-2-(6-fluoro-3,3-dimethyl-1-indanylidene)acetic acid as a white crystalline solid, m.p., 202°–203.5° C.;

h) Preparation of (E)-2-(6-Fluoro-3,3-dimethyl-1-indanylidene)acetyl Chloride

To an ice cold, stirred suspension of (E)-2-(6-fluoro-3,3-dimethyl-1-indanylidene)acetic acid (9.0 g, 0.0409 mol) in dichloromethane (200 ml) was added oxalyl chloride (15.6 g, 0.123 mol, Aldrich). The stirring suspension was allowed to warm to 25° C. during 2 h. The resulting solution was concentrated by spin evaporation in vacuo with the addition of dichloromethane (4×75 ml) to give (E)-2-(6-fluoro-3,3-dimethyl-1-indanylidene)acetyl chloride as an uncharacterized oil. Dichloromethane (approximately 70 g) was added to dissolve this residual oil and the resulting solution was divided equally and used without other purification in Examples 15i, 16 and 17.

i) Preparation of (E)-2-(6-Fluoro-3,3-dimethyl-1-indanylidene)acetamide

A solution of 30% aqueous ammonium hydroxide (10 ml, 76 mmol, Mallinckrodt) was added to the solution of (E)-2-(6-fluoro-3,3-dimethyl-1-indanylidene)acetyl chloride (0.01363 mol) obtained from Example 41h diluted with dichloromethane (200 ml) and cooled to 0° C. The biphasic solution was stirred rapidly and allowed to warm to room temperature over 18 h. The reaction solution was concentrated by spin evaporation in vacuo, diluted with dichloromethane (200 ml), and washed with IN aqueous hydrochloric acid (McIntosh), a solution of 5% aqueous sodium bicarbonate (Mallinckrodt), dried with magnesium sulfate (Mallinckrodt), and concentrated by spin evaporation in vacuo. The residue was chromatographed on Silica Gel 60 using ethyl acetate-hexanes (1:1), and then ethyl acetate. Fractions containing (E)-2-(6-fluoro-3,3-dimethyl-1-indanylidene) acetamide were combined and concentrated by spin evaporation in vacuo. Recrystallization from dichloromethane-hexanes gave 2.85 g (95%) of (E)-2-(6fluoro-3,3-dimethyl-1-indanylidene)acetamide as a white crystalline solid, m.p., 167°–168° C.;

EXAMPLE 16

Preparation of (E)-2-(6-Fluoro-3,3-dimethyl-1-indanylidene)-N-methylacetamide

This compound was prepared in an analogous manner to Example 15i with the replacement of the solution of 30% aqueous ammonium hydroxide with a 40% aqueous solution of methylamine (10 ml, Aldrich). Recrystallization from dichloromethane-hexanes gave 2.89 g (91%) of (E)-2-(6-fluoro-3,3-dimethyl-1-indanylidene)-N-methylacetamide as a white crystalline solid, m.p., 157°–158° C.;

EXAMPLE 17

Preparation of (E)-N-Cyclopropyl-2-(6-fluoro-3,3-dimethyl-1-indanylidene)acetamide This compound was prepared in an analogous manner to Example 15i with the replacement of the solution of 30% aqueous ammonium hydroxide with cyclopropyl amine (4 ml, Aldrich). Recrystallization from dichloromethane-hexanes gave 2.86 g (81%) of (E)-N-cyclopropyl-2-(6-fluoro-3,3-dimethyl-1-indanylidene)acetamide as a white crystalline solid, m.p., 149°–150° C.;

EXAMPLE 18

Preparation of (E)-2-(6-Fluoro-3-methyl-1-indanylidene)acetamide a) Preparation of Ethyl 4-Fluorocinnamate A solution of butyl lithium, 2.5M in hexanes (159 ml, 0.3975 mol, Aldrich), was added dropwise over 0.25 hr, with rapid mechanical stirring, to a solution of triethyl phosphonoacetate (89.2 g, 0.389 mol, Aldrich) in tetrahydrofuran (800 ml, anhydrous, Aldrich) at <5° C. while blanketed with a nitrogen atmosphere. This solution was stirred for an additional 0.25 hr and cooled to 0° C. with an ice bath and a solution of 4'-fluoroacetophenone (50 g, 0.362 mol, Aldrich) in tetrahydrofuran (50 ml) was then added in one portion. Stirring was continued for 18 hr without additional cooling. The solution was then concentrated to ~100 ml by spin evaporation in vacuo and diluted to 500 ml with ethyl acetate. After washing with deionized water (3×50 ml) this solution was concentrated by spin evaporation in vacuo. Distillation at reduced pressure gave 48 g (63%) of ethyl 4-fluorocinnamate as a mixture of (E) to (Z) isomers (ratio 3:1) contaminated with 16% of triethyl phosphonacetate as a clear oil, b.p., 138- 143° C. at 14 Torr;

b) Preparation of Ethyl 3-(4-Fluorophenyl)butyrate

A mixture of ethyl 4-fluorocinnamate (47.5 g, 0.228 mol) and 10% palladium on carbon (0.85 g, Aldrich) in 95% ethanol was shaken in a Parr hydrogenator under 2–3 atm of $H_2$ pressure for 1 h. The mixture was filtered and concentrated by spin evaporation in vacuo. Fractional distillation gave 46.5 g (97%) of ethyl 3-(4-fluorophenyl)butyrate as a clear oil, b.p., 122°–128° C.: c) Preparation of 3-(4-Fluorophenyl)butanoic Acid.

c) Preparation of 3-(4-Fluorophenyl)butanoic Acid

A solution of ethyl 3-(4-fluorophenyl)butyrate (45.3 g, 0.215 mol), 85% potassium hydroxide (14.22 g, 0.215 mol, Mallinckrodt) in 200 ml of deionized water was refluxed for 2 h, concentrated by spin evaporation in vacuo, made acidic (pH 3) with 12N hydrochloric acid (Mallinckrodt), and extracted with dichloromethane (4×200 ml). The dichloromethane layers were combined, washed with deionized water (50 ml), and concentrated by spin evaporation in vacuo. The residue was crystallized from dichloromethane-hexanes to give 34.5 g (88%) of 3-(4-fluorophenyl)butyric acid as a white crystalline solid;

d) Preparation of 3-(4-Fluorophenyl)butyryl Chloride

Oxalyl chloride (71 g, 48.8 ml, 0.560 mol, Aldrich) was added to a mixture of 3-(4-fluorophenyl)butyric acid (34 g, 0.187 mol) in 200 ml of dichloromethane at −5° C. After stirring for 20 min at this temperature, the solution was allowed to warm to 25° C. and stirring was continued for 2 h. The volatiles were removed by spin evaporation in vacuo with the addition of dichloromethane (4 ×) during concentration to give 35.1 g (94%) of 3-(4-fluorophenyl)butyryl chloride as a light yellow oil;

e) Preparation of 6-Fluoro-3-methyl-1-indanone

This compound was prepared in an analogous manner to Example 15e with the replacement of 3-(4-fluorophenyl)-3-methyl-butyryl chloride with 3-(4-fluorophenyl)butyryl chloride (35.1 g, 174.9 mmol). Removal of the volatiles from the combined washes by spin evaporation in vacuo gave 26.3 g (92%) of 6-fluoro-3-methyl-1-indanone as an oil which formed low melting crystals on standing;

f) Preparation of Ethyl 2-(6-Fluoro-1-hydroxy-3-methyl-1-indanyl)acetate

This compound was prepared in an analogous manner to Example 15f with the replacement of 6-fluoro-3,3-dimethyl-I -indanone with 6-fluoro-3-methyl-1-indanone (25 g. 140 mmol). Removal of the volatiles from the workup solution gave 15.0 g (45%) of ethyl 2-(6-fluoro-1-hydroxy-3-methyl-1-indanyl)acetate as a light tan oil;

g) Preparation of (E)-2-(6-Fluoro-3-methyl-1-indanylidene) acetic Acid

This compound was prepared in an analogous manner to Example 15g with the replacement of ethyl 2-(6-fluoro-1-hydroxy-3,3-dimethyl-1-indanyl)acetate with ethyl 2-(6-fluoro-1-hydroxy-3-methyl-1-indanyl)acetate (15 g, 59.5 mmol). Removal of the volatiles from workup gave 9.3 g (76%) of (E)-2-(6-fluoro-3-methyl-1-indanylidene)acetic acid as a tan solid, m.p., 175°–177° C.;

h) Preparation of (E)-2-(6-Fluoro-3-methyl-1-indanylidene) acetyl Chloride

This compound was prepared in an analogous manner to Example 15h with the replacement of (E)-2-(6-fluoro-3,3-dimethyl-1-indanylidene)acetic acid with (E)-2-(6-fluoro-3-methyl-1-indanylidene)acetic acid (9 g, 43.6 mmol). The product residue was dissolved in dichloromethane and used, without purification, in Example 17, 18, and 19.

i) Preparation of (E)-2-(6-Fluoro-3-methyl-1-indanylidene) acetamide

This compound was prepared in an analogous manner to Example 15i with the replacement of (E)-2-(6-fluoro-3,3-dimethyl-1-indanylidene)acetyl chloride with (E)-2-(6-fluoro-3-methyl-1-indanylidene)acetyl chloride (3.26 g, 14.5 mmol). Recrystallization from dichloro- methanehexanes gave 2.39 g (77%) of (E)-2-(6-fluoro-3-methyl-1-indanylidene)acetamide as a white crystalline solid, m.p., 149°–151° C.;

EXAMPLE 19

Preparation of (E)-2-(6-Fluoro-3-methyl-1-indanylidene)-N-methylacetamide

This compound was prepared in an analogous manner to Example 16 with the replacement of (E)-2-(6-fluoro-3,3-dimethyl-1-indanylidene)acetyl chloride with (E)-2-(6-fluoro-3-methyl-1-indanylidene)acetyl chloride (3.26 g, 14.5 mmol). Recrystallization from dichloro- methanehexanes gave 2.27 g (71%) of (E)-2-(6-fluoro-3-methyl-1-indanylidene)N-methylacetamide as a white crystalline solid, m.p., 168°–169° C.;

EXAMPLE 20

Preparation of (E)-N-Cyclopropyl-2-(6-fluoro-3-methyl-1-indanylidene)acetamide

This compound was prepared in an analogous manner to Example 17 with the replacement of (E)-2-(6-fluoro-3,3- dimethyl-1-indanylidene)acetyl chloride with (E)-2-(6-fluoro-3-methyl-1-indanylidene)acetyl chloride (3.26 g, 14.5 mmol). Recrystallization from dichloromethane-hexanes gave 2.30 g (67%) of (E)-N-cyclopropyl-2-(6-fluoro-3-methyl-1-indanylidene)acetamide as a white crystalline solid. m.p., 132°–134° C.;

EXAMPLE 21

Preparation of (Z)-2-(6-fluoro-2-hydroxy-1-indanylidene)acetamide (Method A)

a) Preparation of (Z)-2-(2-bromo-6-fluoro-1-indanylidene) acetamide

N-Bromosuccinimide (22.57 g, 126.8 mmoles, Aldrich) and benzoyl peroxide (1.89 g, 7.8 mmoles, Aldrich) were added to a suspension of (E)-2-(6-fluoro-1-indanylidene) acetamide (21.00 g, 109.8 mmoles) in carbon tetrachloride (400 mL) and benzene (400 mL). The mixture was refluxed under a calcium chloride drying tube while shining an infrared lamp on it for two hours, after which time an orange solution formed. The heat and light were removed, and the solution was stirred at ambient temperature for 18 hours. The mixture was filtered, and the solids were washed with ethyl acetate. The washings and filtrate were combined and evaporated in vacuo. The residue was dissolved in ethyl acetate (800 mL) and washed with water (3×200 mL) and brine (200 mL), dried over sodium sulfate, filtered and evaporated in vacuo. The residue was chromatographed on silica gel eluting first with hexane: ethyl acetate (2:1) gradually increasing the polarity to hexane: ethyl acetate (1:1). The fractions containing the major spot were combined and evaporated in vacuo to give a yellow solid which was dried in a vacuum at 70° C. for 18 hours to give 1.022 g (3%) of (Z)-2-(2-bromo-6-fluoro-1-indanylidene) acetamide as a yellow solid, mp 162°–163° C. $^1$H-NMR b) A mixture of (Z)-2-(2-bromo-6-fluoro-1-indanylidene) acetamide (5.30 g, 19.25 mmoles) and silver nitrate (10.40 g, 61.18 mmoles, Aldrich) in dimethoxyethane (265 mL) and water (100 mL) was refluxed for 18 hours. The mixture was filtered, and the filtrate was diluted with water (700 mL) and extracted with ethyl acetate (6×100 mL). The combined extracts were washed with water (200 mL) and brine (200 mL), dried over magnesium sulfate, filtered, and evaporated in vacuo. The residue was chromatographed on silica gel, eluting with hexane: ethyl acetate (2:1), gradually increasing the polarity to hexane: ethyl acetate (1:1). The fractions containing the compound with Rf=0.18 were combined and evaporated in vacuo to give 1.13 g (28%) of crude (Z)-2-(6-fluoro-2-hydroxy-1-indanylidene)acetamide as an orange solid. Recrystallization from ethyl acetate: hexane mixtures gave 0.49 g (12%) of (Z)-2-(6-fluoro-2-hydroxy-1-indanylidene)acetamide as an off-white solid, mp 201°–202° C.;

c) Preparation of (Z)-2-(6-fluoro-2-hydroxy-1-indanylidene)acetamide (Method B)

A suspension of (E)-2-(6fluoro-1-indanylidene)acetamide (12.00 g, 62.8 mmoles) in dichloromethane (250 mL) was added to a solution of selenium dioxide (5.20 g, 46.9 mmoles, Aldrich) and tert-butyl hydroperoxide (25 mL, 260.8 mmoles, Aldrich) in dichloromethane (500 mL). The suspension was stirred at ambient temperature for 3 days. Additional tert-butyl hydroperoxide (10 mL, 104.3 mmoles) was added, and the mixture was stirred at ambient temperature for 18 hours. Additional selenium dioxide (5.00 g, 45.1 mmoles) was added, and the mixture was stirred at ambient temperature for 18 hours. Additional tert-butyl hydroperoxide (15 mL, 156.5 mmoles) was added, and the mixture was stirred at ambient temperature for 18 hours. The mixture was filtered to remove about one gram of impure product, and the filtrate was dried over magnesium sulfate, filtered, and evaporated in vacuo. Additional selenium dioxide (5.00 g, 45.1 mmoles) was added, and the mixture was stirred at ambient temperature for 18 hours. The mixture was concentrated in vacuo to 300 mL, hexane was added, and the precipitate was collected by filtration, washed with hexane, and combined with the solids collected previously. The combined solids were dissolved in ethyl acetate (700 mL), washed successively with water (3×100 mL) and brine (100 mL), concentrated in vacuo to 100 mL, and cooled in an ice bath. The solids were collected by filtration, and the filtrate was concentrated in vacuo to give a second crop of solids. All of the solids were combined and chromatographed on silica gel, eluting with hexane: ethyl acetate (1:1). The fractions containing the major spot were combined and evaporated in vacuo to give 5.80 g of an off-white solid, which was washed with chloroform (3×50 mL) to give 5.43 g (42%) of (Z)-2-(6-fluoro-2-hydroxy-1-indanylidene) acetamide as a white solid; mp 202°–204° C.;

EXAMPLE 22

(Z)-2-(4,6-Difluoro-2-hydroxy-1-indanylidene) acetamide

A suspension of (E)-2-(4,6-difluoro-1-indanylidene) acetamide (10.0 g, 0.05 mol, prepared as in Example 5g in dichloromethane (250 mL) was added portionwise over a 10 min. period to a mixture of 70% aqueous t-butylhydroperoxide (19.8 mL, 0.15 mol, Aldrich) and selenium dioxide (3.7 g, 0.03 mol, Aldrich) in dichloromethane (500 mL) at ambient temperature. After 18 h, additional t-butylhydroperoxide (10 mL of a 5.0M solution in 2,2,4-trimethylpentane, 0.05 mol, Aldrich) and selenium dioxide (1.8 g, 0.02 mol) were added and the mixture was stirred at ambient temperature. After 18 h, additional t-butylhydroperoxide (10 mL of 70% aqueous solution, 0.08 mol) and selenium dioxide (3.7 g, 0.05 mol) were added and the mixture was stirred at ambient temperature for 8 days. The resulting solid was filtered off and washed with dichloromethane to give 5.85 g of crude (Z)-2-(4,6-difluoro-2-hydroxy-1-indanylidene)acetamide. After 7 days at ambient temperature a second crop of crude (Z)-2-(4,6difluoro-2-hydroxy-1-indanylidene)acetamide was obtained from the filtrate. Column chromatography on silica gel using ethyl acetate as the eluent followed by a second column chromatography on silica gel using ethyl acetate:hexanes (3:2) as eluent and trituration of the resulting solid with pentane gave 2.38 g of (Z)-2-(4,6-difluoro2-hydroxy-1-indanylidene) acetamide as a pink solid: m.p. 235°–237° C.;

EXAMPLE 23

Preparation of (E)-2-(6-fluoro-3-hydroxy-1-indanylidene)acetamide a) Preparation of 3-bromo-6-fluoro-1-indanone A mixture of N-bromosuccinimide (2.76 g, 15.51 mmoles, Aldrich), benzoyl peroxide (0.01 g, 0.04 mmoles, Aldrich) and 6fluoro-1-indanone (2.29 g, 15.25 mmoles) in carbon tetrachloride (20 mL) was refluxed under nitrogen for two hours. The mixture was cooled to ambient temperature, filtered, and the solids were washed with dichloromethane. The washings and filtrate were combined, washed successively with 1.0N sodium hydroxide (2×30 mL), water (2×30 mL) and brine (30 mL), and evaporated in vacuo. The residue was chromatographed on silica gel eluting first with hexane, gradually increasing the polarity to hexane: ethyl acetate (95:5). The fractions containing the major spot were combined and evaporated in vacuo to give a 2.30 g (66%) of 3-bromo-6-fluoro-1-indanone as a yellow oil which was used without further purification.

b) Preparation of 3-hydroxy-6-fluoro-1-indanone

A mixture of 3-bromo-6-fluoro-1-indanone (2.50 g, 10.0 mmoles) and silver carbonate (4.19 g, 15.2 mmoles, Aldrich) in dimethoxyethane (85 mL) and water (65 mL) was stirred overnight at ambient temperature. The mixture was filtered through a pad of celite, and the filtrate was diluted with water (500 mL) and extracted with ethyl acetate (4×100 mL). The combined extracts were washed with water (100 mL) and brine (75 mL), dried over sodium sulfate, filtered, and evaporated in vacuo to give 2.80 g (quantitative) of crude 3-hydroxy-6-fluoro-1-indanone which was used without further purification. Chromatography of 0.41 g on silica gel, eluting with hexane: ethyl acetate (3:4) gave 0.050 g of analytically pure 3-hydroxy-6-fluoro-1-indanone as a tan solid, mp 73°–76° C.;

c) Preparation of 3-((tert-butyldimethylsilyl)oxy)-6-fluoro-1-indanone

A solution of 3-hydroxy-6-fluoro-1-indanone (4.09 g, 24.6 mmoles) in dimethylformamide (10 mL) was added to a solution of tert-butyldimethylsilyl chloride (4.60 g, 30.5 mmoles, Aldrich) and imidazole (4.22 g, 62.0 mmoles, Aldrich) in dimethylformamide (20 mL). The solution was stirred at ambient temperature for 18 hours and evaporated in vacuo. The residue was dissolved in dichloromethane (200 mL) and washed with water (6×75 mL) and brine (100 mL), dried over magnesium sulfate, filtered and evaporated in vacuo. The residue was chromatographed on silica gel eluting with hexane: ethyl acetate (95:5). The fractions containing the major spot were combined and evaporated in vacuo, and the residue was dried in a vacuum at ambient temperature for 18 hours to give 4.14 g (60%) of 3-((tert-butyldimethylsilyl)oxy)-6-fluoro-1-indanone as a white solid, mp 56°–58° C.;

d) Preparation of Ethyl 2-(3-((tert-butyldimethylsilyl)oxy)-6-fluoro-1-hydroxy-1-indanyl) acetate A solution of ethyl acetate (1.00 mL, 10.3 mmoles) and lithium diisopropylamine [This salt was prepared from diisopropylamine (1.41 mL, 10.0 mmoles, Aldrich) and n-butyl lithium (4.00 mL of a 2.5M hexane solution, 10.0 mmoles, Aldrich)], in tetrahydrofuran (15 mL) was stirred at −78° C. under nitrogen for 15 minutes. A solution of 3-((tert-butyldimethylsilyl)oxy)-6-fluoro-1-indanone (2.80 g, 10.0 mmoles) in tetrahydrofuran (15 mL) was added dropwise over a 7 minute period, and the solution was stirred at −78° C. under nitrogen for 1.5 hours. A solution of ammonium chloride (1.60 g, 30.0 mmoles) in water (9 mL) was added, and the resulting suspension was allowed to warm to ambient temperature. The layers were separated, and the aqueous layer was extracted with ether (2×100 mL). The organic extracts were combined and washed successively with water (100 mL) and brine (100 mL), dried over magnesium sulfate, filtered and evaporated ii vacuo. The residue was chromatographed on silica gel eluting with hexane: ethyl acetate (98:2), gradually increasing the polarity to hexane: ethyl acetate (4:1). The fractions containing the major spot were combined and evaporated in vacuo, and the residue was dried in a vacuum at ambient temperature for 18 hours at 60° C. to give 2.86 g (78%) of ethyl 2-(3-((tert-butyldimethylsilyl)oxy)-6-fluoro-1-hydroxy-1-indanyl) acetate as a clear oil;

e) Preparation of (E)-Ethyl 2-(3-((tert-butyldimethylsilyl)oxy)-6-fluoro-1-indanylidene) acetate A solution of ethyl 2-(3-((tert-butyldimethylsilyl)oxy)-6-fluoro-1-hydroxy-1-indanyl) acetate (2.80 g, 7.6 mmoles) was added to a solution of bis[2,2,2-trifluoro-1-phenyl-1-(trifluoromethyl)-ethoxy]diphenylsulfurane (6.30 g, 9.4 mmoles, Fluka) in dichloromethane (50 mL) under a nitrogen atmosphere. The solution was stirred at ambient temperature for 35 minutes and poured into water (500 mL). The organic layer was separated, washed with brine (250 mL), dried over magnesium sulfate, filtered and evaporated in vacuo. The residue was chromatographed on silica gel eluting with hexane: ethyl acetate (99:1). The fractions containing the major spot (and also a minor impurity) were combined and evaporated in vacuo to give 2.68 g (quantitative) of crude (E)-ethyl 2-(3-((tert-butyldimethylsilyl)oxy)-6-fluoro-1-indanylidene) acetate as a yellow oil which was used without further purification;

f) Preparation of (E)-2-(3-((tert-butyldimethylsilyl)oxy)-6-fluoro-1-indanylidene acetamide A solution of dimethylaluminum amide was prepared by adding trimethyl aluminum (6.5 mL of a 2.0M toluene solution, 13.0 mmoles, Aldrich) to a solution of ammonium chloride (0.695 g, 13.0 mmoles) in dichloromethane (25 mL) under a nitrogen atmosphere and stirring for 45 minutes at ambient temperature. This solution of dimethylaluminum amide (13.0 mmoles) was added to a solution of (E)-ethyl 2-(3-((tert-butyldimethylsilyl)oxy)-6-fluoro-1-indanylidene) acetate (1.190 g, 3.4 mmoles) in dichloromethane (60 mL) under a nitrogen atmosphere. The mixture was stirred at ambient temperature for 30 minutes and refluxed for 18 hours. After cooling to ambient temperature and then in an ice bath, the mixture was quenched by dropwise addition of 0.5N hydrochloric acid until gas evolution ceased. The solution was diluted with water (50 mL), the layers were separated, and the aqueous layer was extracted with dichloromethane (75 mL). The organic layers were combined, washed successively with water (75 mL) and brine (75 mL), dried over magnesium sulfate, filtered and evaporated in vacuo. The residue was recrystallized from dichloromethane: hexane mixtures to give 0.321 g (29%) of (E)-2-(3-((tert-butyldimethylsilyl)oxy)-6fluoro-1-indanylidene) acetamide as a white solid, mp 160°–165° C.;

g) Preparation of (E)-2-(6-fluoro-3-hydroxy-1-indanylidene)acetamide

A solution of (E)-2-(3-((tert-butyldimethylsilyl)oxy)-6-fluoro-1-indanylidene) acetamide (1.80 g, 5.6 mmoles) and pyridinium p-toluenesulfonate (0.85 g, 3.4 mmoles, Aldrich) in ethanol (65 mL) was heated at 55°–68° C. for 3.5 hours under a nitrogen atmosphere and evaporated in vacuo. The residue was dissolved in ethyl acetate (150 mL) and washed successively with water (2×150 mL) and brine (150 mL), dried over magnesium sulfate, filtered and evaporated in vacuo. The residue was chromatographed on silica gel eluting with ethyl acetate, gradually increasing the polarity to ethyl acetate: ethanol (95:5). The fractions containing the major spot were combined and evaporated in vacuo, and the residue was dried in a vacuum at 80° C. for 18 hours to give 0.72 g (62%) of (E)-2-(6-fluoro-3-hydroxy-1-indanylidene) acetamide as a white solid, mp 166°–168° C.;

EXAMPLE 24

Preparation of (Z)-2-(2.3-dihydroxy-6-fluoro-1-indanylidene) acetamide a) Preparation of (Z)-2-(2,3-dibromo-6-fluoro-1-indanylidene)acetamide N-Bromosuccinimide (49.37 g, 277.4 mmoles, Aldrich) and benzoyl peroxide (1.60 g, 6.6 mmoles, Aldrich) were added to a suspension of (E)-2-(6-fluoro-1-indanylidene) acetamide (17.68 g, 92.5 mmoles) in carbon tetrachloride (335 mL) and benzene (335 mL). The mixture was refluxed under a calcium chloride drying tube for four hours, after which time an orange solution formed. The heat was removed, and the solution was stirred at ambient temperature for 18 hours. The mixture was filtered, and the solids were washed with ethyl acetate. The washings and filtrate were combined and evaporated in vacuo. The residue was dissolved in ethyl acetate (800 mL) and washed with water (3×200 mL) and brine (200 mL), dried over sodium sulfate, filtered and evaporated in vacuo. The residue was chromatographed on silica gel eluting with hexane: ethyl acetate (2:1). The fractions containing the compound with Rf =0.4 in hexane : ethyl acetate (1:1) were combined and chromatographed again on silica gel eluting with hexane: ethyl acetate (2:1). The fractions containing the compound with Rf=0.4 in hexane: ethyl acetate (1:1) were combined and evaporated in vacuo to give a solid which was washed with hexane and dried in a vacuum at 50° C. for 18 hours to give 1.35 g (4%) of (Z)-2-(2,3-dibromo-6-fluoro-1-indanylidene) acetamide as a yellow solid, mp 158°–163° C. (decomposed).

b) A mixture of (Z)-2-(2,3-dibromo-6-fluoro-1-indanylidene)acetamide (0.54 g, 1.55 mmoles) and silver carbonate (0.56 g, 2.03 mmoles, Aldrich) in dimethoxyethane (15 mL) and water (30 mL) was refluxed for 6 hours. The mixture was stirred overnight at ambient temperature and refluxed again for 6 hours. The mixture was diluted with water (100 mL) and extracted with ethyl acetate (6×30 mL). The combined extracts were washed with water (100 mL) and brine (100 mL), and evaporated in vacuo. The residue was chromatographed on silica gel, eluting with hexane: ethyl acetate (2:1). The fractions containing the compound with Rf=0.15, eluting with ethyl acetate, were combined and evaporated in vacuo to give 0.12 g (35%) of crude (Z)-2-(2,3-dihydroxy-6-fluoro-1-indanylidene) acetamide as a beige solid. Recrystallization from ethyl acetate: hexane mixtures gave 0.037 g (11%) of (Z)-2-(2,3-dihydroxy-6-fluoro-1-indanylidene)acetamide as an off-white solid which was shown by $^1$H-NMR to be a mixture (85:15) of diastereomers, mp 212°–220° C.; $^1$H-NMR (DMSO-$d_6$): d 7.82 (d, 2H), 7.28–7.76 (m, 3H), 6.96 (s, 1H), 6.80 (s, 0.15H), 6.54 (s, 0.85H), 6.51 and 6.12 (m, 0.3H), 5.92 (d, 1H), 4.81 (m, 1.7H); steady-state nOe: irradiation at 6.47 d, observed 20% nOe at 7.38 d.

EXAMPLE 25

Preparation of (E)-2-(6-Fluoro-3-oxo-1-indanylidene)acetamide a) Preparation of (E)-Ethyl 3-fluorocinnamate This compound was prepared in an analogous manner to Example 18a with the replacement of 4'-fluoroacetophenone with 3-fluorobenzaldehyde (33.6 g, 0.3 mmol Aldrich). Distillation gave 32.85 g (56%) of (E)-ethyl 3-fluorocinnamate in 5 fractions (b.p., 140°–155° C. at 15 Torr) which were equally contaminated with approximately 13% of triethyl phosphonoacetate. This material was used without additional purification. $^1$H NMR (DMSO-$d_6$): d 7.66–7.47 (m, 2H), 7.45–7.40 (m, 1H), 7.27–7.20 (m, 1H), 6.70 (d, 1H, $J_{HH}$=16 Hz), 4.18 (q, 2H, $J_{HH}$=7.2 Hz), 4.10–3.96 (m, 0.78H), 3.77 (d, 0.26H, $J_{PH}$=21.3 Hz), 1.24 (t, 3H, $J_{HH}$=7.0 Hz), 1.24–1.14 (m, 1.17H).

b) Preparation of Diethyl 2-carbethoxy-3-(3-fluorophenyl) glutarate

Sodium metal (0.388 g, 0.0169 mol) was stirred in diethyl malonate (15.28 g, 0.0953 mol, Aldrich) under a nitrogen atmosphere at 120° C for 0.33 hr. To the resulting solution was added (E)-ethyl 3-fluorocinnamate (16.4 g, 0.0845 mol) and stirring was continued for 7 hrs at the same temperature. The dark solution was cooled, dissolved in dichloromethane (500 ml) and made acidic with 30 ml of 1N aqueous hydrochloric acid (Macintosh). The volatiles were removed from the resulting froth by spin evaporation in vacuo and the residue was dissolved in ethyl acetate. This solution was washed with 5% aqueous sodium bicarbonate until neutral, water, and the volatiles were removed by spin evaporation in vacuo. Distillation gave 20 g of a material boiling between 130°–185° C. at 0.150 Torr. Redistillation gave 14.72 g (44%) of diethyl 2-carbethoxy-3-(3-fluorophenyl)glutarate as a clear liquid: b.p., 155°–160° C. at 0.1 Torr;

c) Preparation of 3-(3-Fluorophenyl)glutaric acid

To a hot solution of sodium hydroxide (19.15 g, 0.479 mol) in water (50 ml) was added a solution of diethyl 2-carbethoxy-3-(3-fluorophenyl)glutarate (18.8 g, 0.0532 mol) in ethanol (36 ml). The resulting slurry was refluxed for 5 hrs. The mixture was poured into icewater and the ethanol was removed by spin evaporation in vacuo. The residual aqueous solution was acidified with concentrated hydrochloric acid (12N) and the solution (200 ml) was extracted with ethyl acetate (3×300 ml). The ethyl acetate layers were combined, washed with water (50 ml) and the volatiles were removed by spin evaporation in vacuo to give a solid that was recrystallized from dichloromethane and hexanes to give 9.3 g (77%) of 3-(3-fluorophenyl)glutaric acid a white solid; m.p., 126°–127.5° C.;

d) Preparation of 2-(6-Fluoro-3-oxo-1-indanyl)acetic acid

Polyphosphoric acid (39.6 g, Aldrich) and 3-(3-fluorophenyl)glutaric acid (6.6 g, 0.0292 mol) were combined and the mixture heated with an oil bath at 120° C. for 10 min. The now red solution was cooled to approximately 60° C. and water (approximately 100 ml) was added dropwise, with efficient stirring. The resulting precipitate was collected and washed with water. Recrystallization from dichloromethane and hexanes gave 5.3 g (87%) of 2-(6-fluoro-3-oxo-1-indanyl)acetic acid: m.p., 150°–151° C.;

e) Preparation of 2-(6-Fluoro-3-oxo-1-indanyl)acetyl chloride

Oxalyl chloride (4.5 g, 0.035 mol, Aldrich) was added to an ice cold stirring mixture of 2-(6-fluoro-3-oxo-1-indanyl) acetic acid (5.0 g, 0.024 mol) in dichloromethane (200 ml) under a nitrogen atmosphere. The mixture was allowed to warm to room temperature and stirring was continued for 48 hrs. The volatiles were removed from the solution by spin evaporation in vacuo with the addition of dichloromethane (3×50 ml) to give 2-(6-fluoro-3-oxo-1-indanyl)acetyl chloride which was used without purification or analysis.

f) Preparation of 2-(6-Fluoro-3-oxo-1-indanyl)acetamide

A solution of 2-(6-fluoro-3-oxo-1-indanyl)acetyl chloride (prepared from 0.024 mol of 2-(6-fluoro-3-oxo-1-indanyl) acetic acid) in dichloromethane (150 ml) was cooled to 0C and stirred rapidly while 50 ml of ammonium hydroxide, 28–30%, was added. The resulting mixture was allowed to warm to room temperature and stirring was continued for 18 hr. The volatiles from this mixture were removed by spin evaporation in vacuo and the residue was dissolved in dichloromethane (250 ml) and washed with water (3×50 ml). The dichloromethane phase was then slurried with Silica Gel 60 and the volatiles were removed by spin evaporation in vacuo. This silica was then applied to a column of Silica Gel 60 (51×400 mm) wet with dichloromethane and the product was removed by elution with methanol:dichloromethane (3:97) to give, after recrystallization from methanol, 2.4 g (48%) of 2-(6-fluoro-3-oxo-1-indanyl)acetamide as a yellow solid: m.p., 150°–152° C.;

g) Preparation of (E)2-(6-Fluoro-3-oxo-1-indanylidene) acetamide

A mixture of 2-(6-fluoro-3-oxo-1-indanyl)acetamide (0.750 g, 0.0036 mol), N-bromosuccinimide (0.750 g, 0.0042 mol, Aldrich), benzoyl peroxide (0.270 g, 0.0011 mol, Aldrich) in tetrachloromethane (37 ml) and benzene (37 ml) was stirred while heating with an oil bath at 120° C. for 20 min. This reaction was combined with a similarly run reaction (except 0.0024 mol scale). The solution was slurried with Silica Gel 60 and the volatiles were removed by spin evaporation in vacuo. This silica gel was then applied to a column of Silica Gel 60 (51×450 mm) wet with dichloromethane and the product was removed by elution with methanol:dichloromethane (3:97). After the volatiles were removed from the combined fractions containing product by spin evaporation in vacuo, the residue was recrystallized from methanol to give 0.81 g (58%) of (E)-2-(6-fluoro-3-oxo-1-indanylidene)acetamide: m.p., 235° C. (dec.):

EXAMPLE 26

Preparation of (E)-N-Cyclopropyl-2-(6-fluoro-3-ethyl-1-indanylidene)acetamide a) Preparation of Ethyl 3-(4-fluorophenyl)pentenoate A solution of butyllithium, 1.6M in hexanes (230 ml, 0.368 mol, Aldrich) was added dropwise over 0.5 hr, with rapid mechanical stirring, to a solution of triethyl phosphonoacetate (78.9 g, 0.351 mol, Aldrich) in tetrahydrofuran (800 ml, anhydrous, Aldrich) at <5° C. while blanketed with a nitrogen atmosphere. This solution was stirred for an additional 0.25 hr and cooled to −5° C. with a methanol:ice bath and a solution of 4'-fluoropropiophenone (50 g, 0.328 mol, Aldrich) in tetrahydrofiran (50 ml) was then added in one portion. Stirring was continued for 18 hr without additional cooling. The solution was concentrated to a golden yellow sludge by spin evaporation in vacuo and diluted to 1000 ml with ethyl acetate. After washing with deionized water (3×100 ml) this solution was concentrated by spin evaporation in vacuo. Distillation at reduced pressure gave 45.65 g (63%) of ethyl 3-(4-fluorophenyl)pentenoate as a mixture of (E) and (Z) isomers (ratio 1:1) contaminated with 30% of triethyl phosphonoacetate as a clear liquid, b.p. 140°–146° C. at aspirator pressure;

b) Preparation of Ethyl 3-(4-Fluorophenyl)valerate

A mixture of ethyl 3-(4-fluorophenyl)pentenoate (45.65 g, 0.137 mol) and 10% palladium on carbon (0.86 g, Aldrich) in 95 % ethanol was shaken under 4 atm hydrogen pressure in a Parr hydrogenator for 1.5 hr. The mixture was filtered and concentrated by spin evaporation in vacuo. Fractional distillation gave 38.95 g (63%) of ethyl 3-(4-fluorophenyl) valerate as a clear oil contaminated with 29% triethyl phosphonoacetate. b.p., 133°–142° C. at 17 mm Hg;

c) Preparation of 3-(4-Flurophenyl)valeric acid

This compound was prepared in an analogous manner to Example 18c with the replacement of 3-(4-fluorophenyl) butyrate with ethyl 3-(4-fluorophenyl)valerate (38.95 g 0.144 mol, containing 29% triethyl phosphoneacetate) and using an excess of 85% potassium hydroxide (18.05 g, 0.273 mol, Mallinckrodt). The dichloromethane layers were combined, washed with deionized water (50 ml) and concentrated by spin evaporation in vacuo. The residue was crystallized from hexanes to give 23.47 g (83%) of 3-(4-flurophenyl)valeric acid as a white crystalline solid: NMR (DMSO-$d_6$): d 12 (s, 1H), 7.28–7.24 (m, 2H), 7.14–7.08 (m, 2H), 2.91–2.89 (m, 1H), 2.64–2.41 (m, 2H), 1.66–162 (m, 1H), 1.56–1.51 (m, 1H), 0.71 (t, 3H, J=7.3 Hz).

d) Preparation of 3-(4-Fluorophenyl)valeroyl chloride

This compound was prepared in an analogous manner to Example 18d with the replacement of 3-(4-fluorophenyl) butyric acid with 3-(4-fluorophenyl)valeric acid (23.47g, 0.120 mol). The volatiles were removed by spin evaporation in vacuo with the addition of dichloromethane (6×250 ml) during concentration to give 25.25 g (98%) of 3-(4-fluorphenyl)valeroyl chloride as a golden yellow liquid: NMR (DMSO-$d_6$): d 7.3–7.22 (m, 2H), 7.15–7.06 (m, 2H), 2.98–2.73 (m, 1H), 2.66–2.38 (m, 2H), 1.74–1.37 (m,2H), 0.70 (t, 3H, J=7.2 Hz).

e) Preparation of 3-Ethyl-6-fluoro-1-indanone

This compound was prepared in an analogous manner to Example 18e with the replacement of 3-(4-fluorophenyl) butyryl chloride with 3-(4-fluorophenyl)valeroyl chloride (25.27 g, 0.118 mol). The dichloromethane extractions were combined, washed with deionized water (100 ml) and concentrated by spin evaporation in vacuo The residue was chromatographed on Silica Gel 60 using a step gradient going from hexanes to ethyl acetate:hexanes/1:1. Fractions containing 3-ethyl-6-fluoro-1-indanone were combined and concentrated by spin evaporation in vacuo with dichloromethane (2×150 ml) added during concentration to give 17.48 g (83%) of 3-ethyl-6-fluoro-1-indanone as a canary yellow syrup: NMR (DMSO-$d_6$): d 7.74–7.7 (dd, 1H, $J_{HF}$=8.4 Hz, $J_{HH}$=4.8 Hz), 7.6–7.53 (ddd, 1H, $J_{HF}$=9.0 Hz, $J_{HH}$=9.0 Hz and 2.7 Hz), 7.37 (dd, 1H, $J_{HF}$=7.8 Hz, $J_{HH}$=2.4 Hz), ~3.3(m, 1H, partially obscured by water), 2.88 (dd,1H, $J_{gem}$=19.2 Hz, J=7.6 Hz), 2.39 (dd, 1H, $J_{gem}$=19.2 Hz, J=2.4 Hz), 1.98–1.90 (m, 1H), 1.54–1.44 (m, 1H), 0.90 (t, 3H, J=7.3 Hz).

f) Preparation of cis and trans Ethyl 2-(3-ethyl-6-fluoro-1-hydroxy-1-indanyl)acetate This compound was prepared in an analogous manner to Example 18f with replacement of 6-fluoro-3-methyl-1-indanone with 3-ethyl-6-fluoro-1-indanone (17.3 g, 0.097 mol). Removal of the volatiles from the workup solution gave 25.17 g (97%) of cis and trans ethyl 2-(3-ethyl-6-fluoro-1 -hydroxy-1-indanyl)acetate as a golden yellow oil: NMR (DMSO-$d_6$): d 7.23–7.21 (m,1H), 7.13–7.06 (m, 2H), 5.48 (s, 1H), 4.0 (q, 2H, J=7.2 Hz), 2.90–2.82 (m, 1H), 2.80–2.73 (m, 1H), 2.70–2.55 (m, 2H), 2.04–1.9 (m,1H), 1.83–167 (m, 1H), 1.46–1.28 (m, 1H), 1.11 (t,3H, J=7.1 Hz), 0.95 (t, 3H, J=7.3 Hz).

g) Preparation of (E)-2-(3-Ethyl-6-fluoro-1-indanylidene) acetic acid

This compound was prepared in an analogous manner with Example 18g with the replacement of ethyl 2-(6-fluoro-1-hydroxy-3-methyl-1-indanyl)acetate with ethyl 2-(3-ethyl-6-fluoro-1-hydroxy-1-indanyl)acetate (24.85 g, 0.093 mol). Removal of the volatiles from the workup gave a beige residue. Recrystallization from dichloromethane-hexanes gave 12.91 g (63%) of (E)-2-(3-ethyl-6-fluoro-1-indanylidene)acetic acid as a white crystalline solid, m.p., 145°–148° C.;

h) Preparation of (E)-2-(3-ethyl-6-fluoro-1-indanylidene) acetyl chloride

This compound was prepared in an analogous manner to Example 18h with replacement of (E)-2-(6-fluoro-3-methyl-1 -indanylidene)acetic acid with (E)-2-(3-ethyl-6-fluoro-1-indanylidene)acetic acid (5.7 g. 25.88 mmol). The product residue was dissolved in dichloromethane and used without purification in Example 26.

i) Preparation of (E)-N-Cyclopropyl-2-(6-fluoro-3-ethyl-1-indanylidene)acetamide This compound was prepared in an analogous manner to Example 20 with the replacement of (E)-2-(6fluoro-3-methyl-1-indanylidene)acetyl chloride with (E)-2-(3-ethyl-6-fluoro-1-indanylidene)acetyl chloride (3.18 g, 13.3 mmol). Recrystallization from dichloromethane-hexanes gave 2.24 g (65%) of (E)-N-cyclopropyl-2-(6-fluoro-3-ethyl-1-indanylidene)acetamide as a white crystalline solid, m.p., 143°–147° C.;

EXAMPLE 27

Preparation of (E-N-Cyclopropyl-2-(6-fluoro-3-propyl-1-indanylidene)acetamide a) Preparation of 4' fluorobutyrophenone Aluminum chloride (139 g, 1.04 mol) was added to a solution of butyryl chloride (55.45 g, 0.520 mol, Aldrich) in dichloromethane (500 ml) stirring under a nitrogen atmosphere at 25° C. A solution of fluorobenzene (50.1 g, 0.521 mol, Aldrich) in dichloromethane was added and stirring was continued for 18 h. The reaction solution was poured over ice and extracted with dichloromethane (3×400 ml). The combined dichloromethane extractions were washed with deionized water (2×250 ml), 1.0N hydrochloric acid (500 ml), saturated sodium bicarbonate solution (2×500 ml) and deionized water ( 4×250 ml),concentrated by spin evaporation in vacuo. This material was combined with material from a similar preparation (using 0.26 mol of fluorobenzene) for distillation. Distillation at reduced pressure gave 69.27 g (53%) of 4'-fluorobutyrophenone as a pale yellow liquid which later partially crystallized, b.p. 108°–112° C. at 30 millitorr: NMR (DMSO-$d_6$): d 8.03 (q, 2H, J=9.0 Hz and 5.6 Hz), 7.31 (t, 2H, J=8.9 Hz), 2.97 (t, 2H, J=7.0 Hz), 1.65–1.55 (m, 2H), 0.91 (t, 3H, J=7.3 Hz).

b) Preparation of Ethyl 3-(4-fluorophenyl)hexenoate

A solution of butyllithium, 2.5M in hexanes (166 ml, 0.416 mol, Aldrich) was added dropwise over 0.5 hr, with rapid mechanical stirring, to a solution of triethyl phosphonoacetate (93.2 g, 0.416 mol, Aldrich) in tetrahydrofuran (700 ml, anhydrous,Aldrich) at <5° C. while blanketed with a nitrogen atmosphere. This solution was stirred for an additional 0.25 hr and cooled to –5° C. with a methanol:ice bath and a solution of 4'-fluorobutyrophenone (69 g, 0.416 mol, Aldrich) in tetrahydrofuran (150 ml) was then added in one portion. Stirring was continued for 18 hr without additional cooling. The solution was concentrated to a dark camel sludge by spin evaporation in vacuo and diluted to 600 ml with deionized water. The aqueous solution was extracted with dichloromethane (5×500 ml) and the dichloromethane was concentrated by spin evaporation in vacuo. Distillation at reduced pressure gave 58.5 g (60%) of ethyl 3-(4-fluorophenyl) hexenoate as a mixture of (E) and (Z) isomers (ratio 1:1) as clear liquid, b.p. 140°–150° C. at aspirator pressure;

c) Preparation of Ethyl 3-(4-Fluorophenyl)hexanoate

A mixture of ethyl 3-(4-fluorophenyl)hexenoate (58.12 g, 0.246 mol) and 10% palladium on carbon (1.1 g, Aldrich) in 95% ethanol was shaken in a Parr hydrogenator under a pressure of 2–4 atm of hydrogen for 0.75 hr. The mixture was filtered and concentrated by spin evaporation in vacuo to give 58.4 g (99.6%) of ethyl 3-(4-fluorophenyl)hexanoate as a clear liquid, NMR (DMSO-$d_6$): d 7.27–7.20 ( m, 2H), 7.12–7.04 (m, 2H), 3.91 (q, 2H, J=7.2 Hz), 2.99 (m, 1H), 2.66–2.59 (m, 1H), 2.52–2.44 (m, 1H, partially obscured by DMSO), 1.59–1.46 (m, 2H), 1.13–1.07 (m, 2H), 1.02 (t, 3H, J=7.2Hz), 0.78 (t, 3H, J=7.5 Hz).

d) Preparation of 3-(4-Fluorophenyl)hexanoic acid

This compound was prepared in an analogous manner to Example 65c with the replacement of 3-(4-fluorophenyl) valerate with ethyl 3-(4-fluorophenyl) hexanoate (58 g, 0.243 mol). The dichloromethane layers were combined, washed with deionized water (250 ml) and concentrated by spin evaporation in vacuo. The residue was coevaporated with hexanes (200 ml) to give 46.81 g (92%) of 3-(4-fluorophenyl)hexanoic acid as a pale yellow oil;

e) Preparation of 3-(4-Fluorophenyl)hexanoyl chloride

This compound was prepared in an analogous manner to Example 18d with the replacement of 3-(4-fluorophenyl) butyric acid with 3-(4-fluorophenyl)hexanoic acid (46.5 g, 0.222 mol). The volatiles were removed by spin evaporation in vacuo with the addition of dichloromethane (5×250 ml) during concentration to give 50.01 g (99%) of 3-(4-fluorophenyl)hexanoyl chloride as a golden yellow liquid;

f) Preparation of 6-fluoro-3-propyl-1-indanone

This compound was prepared in an analogous manner to Example 18e with the replacement of 3-(4-fluorophenyl) butyryl chloride with 3-(4-fluorophenyl) hexanoyl chloride (49.95 g, 0.218 mol). The dichloromethane extractions were combined, washed with deionized water (250 ml) and concentrated by spin evaporation in vacuo. The residue was coevaporated with dichloromethane (100 ml) to give 41.26 g (98%) of 6-fluoro-3-propyl-1-indanone as a golden yellow syrup;

g) Preparation of cis and trans Ethyl 2-(6-fluoro-1-hydroxy-3-propyl-1-indanyl)acetate This compound was prepared in an analogous manner to Example 18f with replacement of 6-fluoro-3-methyl-1-indanone with 6-fluoro-3-propyl-1-indanone (40.75 g, 0.212 mol). Removal of the volatiles from the workup solution gave 57.48 g (97%) of cis and trans ethyl 2-(6-fluoro-1-hydroxy-3-propyl-1-indanyl)acetate as a golden yellow oil;

h) Preparation of (E)-2-(6-Fluoro-3-propyl-1-indanylidene) acetic acid

This compound was prepared in an analogous manner with Example 18g with the replacement of ethyl 2-(6-fluoro-1-hydroxy-3-methyl-1-indanyl)acetate with ethyl 2-(6-fluoro-1-hydroxy-3-propyl-1-indanyl)acetate (57.12 g, 0.204 mol). Removal of the volatiles from the workup gave a golden yellow residue. The residue was slurried in hexanes to give 24.49 g (51%) of (E)-2-(6-fluoro-3-propyl-1-indanylidene)acetic acid as a white crystalline solid, m.p., 141°–144° C.: NMR (DMSO-$d_6$);

i) Preparation of (E)-2-(6-Fluoro-3-propyl-1-indanylidene) acetyl chloride

This compound was prepared in an analogous manner to Example 18h with replacement of (E)-2-(6-fluoro-3-methyl-1-indanylidnene)acetic acid with (E)-2-(6-fluoro-3-propyl-1-indanylidene)acetic acid (15.01 g, 64.07 mmol). The product residue was dissolved in dichloromethane and used without purification in Example 27j.

j) Preparation of (E)-N-Cyclopropyl-2-(6-fluoro-3-propyl-1-indanylidene)acetamide This compound was prepared in an analogous manner to Example 20 with the replacement of (E)-2-(6-fluoro-3-methyl- I -indanylidene)acetyl chloride with (E)-2-(6-fluoro-3-propyl-1-indanylidene)acetyl chloride (3.26 g, 0.013 mol). The volatiles were removed by spin evaporation in vacuo to give a golden yellow oil. The oil was chromatographed on Silica Gel 60 with a step gradient of hexanes to ethyl acetate-hexanes (1:1). Fractions containing (E)-N-cyclopropyl-2-(6fluoro-3-propyl-1-indanylidene)acetamide were combined and concentrated by spin evaporation in vacuo with hexanes (4×250 ml) added during concentration to give 2.09 g (59%) of (E)-N-Cyclopropyl-2-(6-fluoro-3-propyl-1-indanylidene)acetamide as a white powdery solid, m.p. 94°–97° C.;

EXAMPLE 28

Preparation of (Z)-2-(6-Fluoro-1-indanylidene) acetamide

A solution of (E)-2-(6-fluoro-1-indanylidene)acetamide (20 g,104.6 mmol) in dichloromethane:methanol(3:1) (1000 ml) was irradiated by an Canrad-Hanovia quartz, mercury-vapor photochemical immersion lamp, 450 wattts (Ace Glass, 7825-35) for 0.5 h. The volatiles were removed by spin evaporation in vacuo to give a beige residue. This residue was chromatographed on Silica Gel 60 using a step gradient going from ethyl acetate: hexanes(1:1) to ethyl acetate:ethanol(1:1). Fractions containing (Z)-2-(6-fluoro-1-indanylidene)acetamide were combined and concentrated by spin evaporation in vacuo. The resulting solid was slurried in hexanes to give 7.2 g (37%) of (Z)-2-(6-fluoro-1-indanylidene)acetamide as a white crystalline solid, m.p., 175°–177 ° C.;

EXAMPLE 29

Preparation of (E)-2-(4,6-Difluoro-3-oxo-1-indanylidene)acetamide a) Preparation of 2,4-Dicarbethoxy-3-(3,5-difluorophenyl)-5-hydroxy-5-methyl-1-cyclohexanone Slightly warm, liquid 3,5-difluorobenzaldehyde (5.0 g, 0.0352 mol, Aldrich), 95% ethanol (1.75 ml), and piperidine (0.7 ml) were added, with stirring, to ethyl acetoacetate (9.2 g, 0.0704 mol, Aldrich). The solution was stirred until homogeneous and was then placed in a water bath to control the slightly exothermic reaction. After 4 hrs, the crystalline mass was dissolved in warm dichloromethane (100 ml). Dilution with hexanes (300 ml) gave a turbid solution. After standing for 24 hrs, the crystalline product was collected by filtration and washed with hexanes to give 8.0 g (59%) of 2,4-dicarbethoxy-3-(3,5-difluorophenyl)-5-hydroxy-5-methyl-1-cyclohexanone: m.p., 185°–186° C.;

b) Preparation of 3-(3,5-Difluorophenyl)glutaric acid

To a hot (95° C.) solution prepared from sodium hydroxide (322 g, 8.1 mol) and deionized water (322 ml) was added a mixture of 2,4-diacetyl-3-(3,5-difluorophenyl)-5-hydroxy-5-methyl-1-cyclohexanone (43 g, 0. 112 mol) in ethanol (322 ml) with rapid stirring. The resulting mixture was refluxed for 4 hrs using an oil bath at 140° C. The ethanol was removed by spin evaporation in vacuo and the resulting slurry was cooled with an ice bath, and concentrated hydrochloric acid (12N) was added to adjust the pH to approximately 1. The precipitate was dissolved by the addition of water, and this aqueous solution was extracted with ethyl acetate (total volume 1500 ml). The ethyl acetate extracts were combined, washed with water, dried with $MgSO_4$, and the volatiles were removed by spin evaporation in vacuo. Recrystallization of the residue from dichloromethane and hexanes gave 9.10 g (33%) of 3-(3,5-difluorophenyl)glutaric acid: m.p., 170°–172° C.;

c) Preparation of 2-(4,6-Difluoro-3-oxo-1-indanyl)acetic acid

This compound was prepared in an analogous manner to that of Example 25d with the replacement of 3-(3-fluorophenyl)glutaric acid with 3-(3,5-difluorophenyl) glutaric acid (9.02 g, 36.9 mmol) and an increase of the heating time from 10 min to 30 min. Chromatography of the collected product on a column of Silica Gel 60 (51×450 mm) with methanol: dichloromethane (4:96) gave a material which was recrystallized from water to give 1.93 g (23%) of 2-(4,6-difluoro-3-oxo-1-indanyl)acetic acid: m.p., 170°–172° C.;

d) Preparation of 2-(4,6-difluoro-3-oxo-1-indanyl)acetyl chloride

This compound was prepared in an analogous manner to that of Example 25e with the replacement of 2-(6-fluoro-3-oxo-1-indanyl)acetic acid with 2-(4,6-difluoro-3-oxo-1-indanyl)acetic acid (3.85 g, 0.017 mol). The 2-(4,6-difluoro-3-oxo-1-indanyl)acetyl chloride thus prepared was used without additional purification or analysis.

e) Preparation of 2-(4,6-Difluoro-3-oxo-1-indanyl)acetamide

This compound was prepared in an analogous manner to that of Example 25f with the replacement of 2-(3-fluoro-3-oxo-1-indanyl)acetyl chloride with 2-(4,6-difluoro-3-oxo-1-indanyl)acetic acid (4.2 g, 17 mmol). After chromatography, recrystallization twice from dichloromethane:hexanes gave 2.8 g (77%) of 2-(4,6-Difluoro-3-oxo-1-indanyl)acetamide: m.p., 155°–157° C.;

f) Preparation of (E)-2-(4,6-Difluoro-3-oxo-1-indanylidene)acetamide

A mixture of 2-(4,6-difluoro-3-oxo-1-indanyl)acetamide (1.0 g, 0.0044 mol), N-bromosuccinimide (0.950 g, 0.00533 mol), 2,2'-azobis(2-methylpropionitrile) (0.350 g, 0.00213 mol, Kodak), tetrachloromethane (50 ml) and benzene (50 ml) was heated with an oil bath at 120° C. for 1 hr. The reaction solution was diluted with dichloromethane, slurried with Silica Gel 60, and the volatiles were removed by spin evaporation in vacuo. This silica was then applied to a column of Silica Gel 60 (51×450 mm) wet with dichloromethane and the product was removed by elution with methanol:dichloromethane (2:98). The volatiles were removed by spin evaporation in vacuo to give 0.613 g of a residue. This residue was recrystallized from methanol to give 0.302 g (31%) of (E)-2-(4,6-difluoro-3-oxo-1-indanylidene)acetamide: m.p., 250° C. (dec.);

EXAMPLE 30

Preparation of (E)-N-Ethyl-2-(7-fluoro-1,2,3,4-tetrahydro-1-naphthylidene)acetamide a) Preparation of 2-Chloro-N-ethylacetamide Chloroacetyl chloride (45 g, 398 mmoles, Aldrich) was added dropwise to aqueous ethylamine (70%, 30.7 g, 0.48 mol) in 100 ml of deionised water originally at –20° C. with stirring. The temperature of the reaction was raised to 0° C. and stirring was continued until the reaction was no longer exothermic. The resulting solution was acidified with concentrated hydrochloric acid (7 ml) and extracted with dichloromethane (4×250 ml). The organic layer was washed with deionised $H_2O$ (150 ml) filtered through glass wool and concentrated by spin evaporation in vacuo to give a pale yellow liquid residue. This residue was concentrated with hexanes (200 ml) and dichloromethane (600 ml) to give 16.01 g (59%) of 2-chloro-N-ethylacetamide. The spectra of this compound was consistent with the proposed structure and the compound was used without further analysis.

b) Preparation of Diethyl (N-ethylcarbamoyl)methyl) phosphonate

2-Chloro-N-ethylacetamide (15.5 g, 127.5 mmol) was added in portions with stirring to triethyl phosphite (28 g, 0.17 moles, Aldrich) at 110° C. The solution was then heated to 155° C. for 30 minutes, cooled to 125° C., and the volatiles were removed by distillation under aspirator vacuum (15 mm Hg) at this temperature. Fractional distillation gave 25.06 g (88%) of diethyl ((N-ethylcarbamoyl) methyl) phosphonate; b.p., 135°–147° C. at 0.50 mm Hg. This compound was used without further analysis.

c) Preparation of (E)-N-Ethyl-2-(7-fluoro-1,2,3,4-tetrahydro-1-naphthylidene) acetamide To a stirred suspension of NaH (80% dispersion in mineral oil, 0.91 g, 0.030 mol, Aldrich) in dimethyl sulfoxide (150 ml) at room temperature under a nitrogen atmosphere was added a solution of diethyl ((N-ethylcarbamoyl)methyl phosphonate (6.8 g, 0.030 mol) in dimethyl sulfoxide (50 ml). The reaction was slightly exothermic. The reaction was stirred for 0.75 h. A solution of 7-fluoro-1-tetralone (5.00 g, 0.030 mol) in dimethyl sulfoxide (50 ml) was added and the reaction was stirred for 1 h. The reaction was poured into ice-cold water (300 ml) and extracted with diethyl ether (3×ml). The combined ether phases were washed with water (100 ml) and concentrated by spin evaporation in vacuo to give a golden yellow syrup. This residue was chromatographed on Silica Gel 60 using a step gradient going from ethyl acetate-hexanes/1:3 to ethyl acetate-hexanes/1:1. Fractions containing (E)-N-Ethyl-2-(7-fluoro-1,2,3,4-tetrahydro-1-naphthylidene acetamide were combined and spin evaporated in vacuo to give 3.74 g of a white solid. Recrystallization from dichloromethane-hexanes gave 3.28 g (46%) of (E)-N-ethyl-2-(7-fluoro-1,2,3,4-tetrahydro-1-naphthylidene) acetamide as a fluffy white solid; m.p., 87°–89° C.

Anal.Calcd. for $C_{14}H_{16}FNO$ (mw 233.278): C,72.08; H, 6.91; N, 6.00 Found: C,72.05; H, 6.91; N, 6.05

EXAMPLE 31

Preparation of (Z)-N-Ethyl-2-(7-fluoro-1,2,3,4-tetrahydro-1-naphthylidene)acetamide Fractions from the chromatographic purification described in Example 30 that contained (Z)-N-ethyl-2-(7-fluoro-1,2,3,4-tetrahydro-1-naphthylidene)acetamide were combined and concentrated in vacuo to give 1.07 g (20%) of (Z)-N-ethyl-2-(7-fluoro-1,2,3,4-tetrahydro-1-naphthylidene)acetamide as a while solid; m.p., 117°–118° C.

Anal.Calcd. for $C_{14}H_{16}FNO$ (mw 233.278): C,72.08; H, 6.91; N,6.00. Found: C,71.99; H, 6.89; N,6.01.

EXAMPLE 32

Preparation of (E)-2-(4,6-difluoro-3-hydroxy-1-idanylidene)acetamide

A suspension of (E)-2-(4,6-difluoro-3-oxo-1-indanylidene)acetamide (0.100 g, 0.45 mmol) and sodium borohydride (0.017 g, 0.45 mmol) in 95% ethanol was stirred at ambient temperature for 2 hours. The mixture was cooled in an ice bath and quenched with 0.1N hydrochloric acid (3 mL). The ethanol was evaporated in vacuo, and the residue was dissolved in ethyl acetate (50 mL), washed successively with water (2×3 mL) and brine (30 mL), dried over sodium sulfate, filtered, and evaporated in vacuo. The resudue was washed successively with cold ethyl acetate, hexane, and diethyl ether to give 0.046 g (45%) of (E)-2-(4,6difluoro-3-hydroxy-1-indanylidene)acetamide as a white solid; mp 232°–237° C. (dec.) $^1$H-NMR (DMSO-$d_6$): δ7.06–7.42 (m, 4H), 6.49 (s, 1H), 5.52 (d, 1H), 5.30 (m,1H), 3.44 (m,1H), 3.03 (d, 1H).

The following compounds were prepared by methods similar to those of the indicated Examples

| Ex.No. | Compound | M.p.(°C.) | Method (Ex.No.) |
|---|---|---|---|
| 33 | (E)-2-(6-Fluoro-3-ethyl-1-indanylidene)-N-methylacetamide | 141–143 | 26 |
| 34 | (E)-2-(6-Fluoro-3-ethyl-1-indanylidene)acetamide | 163–166 | 15 |
| 35 | (E)-2-(6-Fluoro-3-ethyl-1-indanylidene)-N-isopropylacetamide | 127–130 | 26 |
| 36 | (E)-2-(6-Fluoro-3-ethyl-1-indanylidene)-N,N-dimethylacetamide | 79–82 | 26 |
| 37 | (E)-2-(6-Fluoro-3-propyl-1-indanylidene)-N-methylacetamide | 105–107 | 26 |
| 38 | (E)-2-(6-Fluoro-3-propyl-1-indanylidene-N,N-dimethylacetamide | 95–97 | 26 |
| 39 | (E)-2-(6-Fluoro-3-propyl-1-indanylidene)-N-isopropylacetamide | 108–110 | 26 |
| 40 | (E)-2-(6-Fluoro-3-propyl-1-indanylidene)acetamide | 167–169 | 15 |
| 41 | (E)-4-(2-(6-Fluoro-1-indanylidene)acetyl)morpholine | 133–136 | 4 |
| 42 | (E)-2-(6-Fluoro-1-indanylidene)-N-isopropylacetamide | 143–145 | 4 |
| 43 | (E)-2-(6-Fluoro-1-indanylidene)-N-methylacetamide | 201–205 | 4 |
| 44 | (E)-N-Cyclobutyl-2-(6-fluoro-1-indanylidene)acetamide | 137–139 | 4 |
| 45 | (E)-2-(6-Fluoro-1-indanylidene)-N-propylacetamide | 82–84 | 4 |
| 46 | (E)-2-(6-Fluoro-1-indanylidene)-N,N-dimethylacetamide | 74–77 | 4 |
| 47 | (E)-N-Cyclopropyl-2-(5,6-difluoro-1-indanylidene)acetamide | 169–171 | 4 |
| 48 | (E)-2-(5,6-Difluoro-1-indanylidene)-N-methylacetamide | 209–211 | 4 |
| 49 | (E)-2-(5,6-Difluoro-1-indanylidene)acetamide | 165–167 | 1 |
| 50 | (E)-2-(5,7-Difluoro-1-indanylidene)acetamide | 161–162 | 1 |
| 51 | (E)-N-Cyclopropyl-2-(5,7-difluoro-1-indanylidene)acetamide | 145–147 | 4 |
| 52 | (E)-2-(5,7-Difluoro-1-indanylidene)-N-methylacetamide | 193–195 | 4 |
| 53 | (E)-2-(4,6-Difluoro-1-indanylidene)-N-isopropylacetamide | 167–170 | 4 |
| 54 | (E)-2-(4,6-Difluoro-1-indanylidene)-N,N-dimethylacetamide | 105–106 | 4 |
| 55 | (E)-2-(4,6-Difluoro-1-indanylidene)-N-ethylacetamide | 130–132 | 4 |
| 56 | (E)-N-Ethyl-2-(4,6-difluoro-1-indanylidene)-N-methylacetamide | 96–98 | 4 |
| 57 | (E)-2-(4,7-Difluoro-1-indanylidene)acetamide | 167–169 | 5 |
| 58 | (E)-2-(4,5-Difluoro-1-indanylidene)acetamide | 195–197 | 5 |
| 59 | (E)-N-Cyclopropyl-2-(4,5-difluoro-1-indanylidene)acetamide | 135–137 | 4 |
| 60 | (E)-N-Cyclopropyl-2-(4,7-difluoro-1-indanylidene)acetamide | 134–136 | 4 |
| 61 | (E)-2-(4,6-Difluoro-1-indanylidene)-N-methylacetamide | 181–183 | 4 |
| 62 | (E)-2-(7-Fluoro-1,2,3,4-tetrahydro-1-naphthylidene)acetamide | 148–150 | 12 |
| 63 | (E)-2-(6-Fluoro-3,4-dihydro-2H-1-benzopyran-4-ylidene)acetamide | 155–157 | 5 |
| 64 | (E )-2-(6-Fluoro-3,4-dihydro-2H-1-benzopyran-4-ylidene)-N-methylacetamide | 182–185 | 4 |
| 65 | (E)-2-(7-Fluoro-1,2,3,4-tetrahydro-1-naphthylidene)-N-methylacetamide | 115–118 | 30 |
| 66 | (E)-2-(7-Fluoro-1,2,3,4-tetrahydro-1-naphthylidene)-N-isopropylacetamide | 144–146 | 30 |
| 67 | (E)-2-(7-Fluoro-1,2,3,4-tetrahydro-1-naphthylidene)-N-propylacetamide | 71–74 | 30 |
| 68 | (E)-N-Cyclobutyl-2-(7-fluoro-1,2,3,4-tetrahydro-1-naphthylidene)acetamide | 159–162 | 30 |
| 69 | (E)-4-(2-(7-Fluoro-1,2,3,4-tetrahydro-1-naphthylidene)acetyl)morpholine | 96–99 | 30 |
| 70 | (E)-N-Ethyl-2-(7-fluoro-1,2,3,4-tetrahydro-1-naphthylidene)-N-methylacetamide | 66–68 | 14 |
| 71 | (Z)-2-(7-Fluoro-1,2,3,4-tetrahydro-1-naphthylidene)acetamide | 198–201 | 31 |
| 72 | (E)- N-Cyclopropyl-2-(6-fluoro-3,4-dihydro-2H-1-benzopyran-4-ylidene)acetamide | 146–148 | 4 |

Pharmaceutical Compositions

In the following Examples 73 to 78 the "Active Ingredient" is a compound of formula (I) or a pharmaceutically acceptable salt or solvate thereof.

EXAMPLE 73

Tablet Compositions

The following compositions A, B and C are prepared by wet granulation of the ingredients with a solution of povidone, followed by addition of magnesium stearate and compression.

|  | mg/tablet | mg/tablet |
|---|---|---|
| Composition A |  |  |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |
| Composition B |  |  |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |
| Composition C |  |  |
| Active ingredient |  | 100 |
| Lactose |  | 200 |
| Starch |  | 50 |
| Povidone |  | 5 |
| Magnesium Stearate |  | 4 |
|  |  | 359 |

The following compositions, D and E, are prepared by direct compression of the admixed ingredients. The lactose in composition E is of the direct compression type (Dairy Crest—"Zeparox").

|  | mg/tablet |
|---|---|
| Composition D |  |
| Active ingredient | 250 |
| Pregelatinized Starch NF15 | 150 |
|  | 400 |
| Composition E |  |
| Active ingredient | 250 |
| Lactose | 150 |
| Avicel | 100 |
|  | 500 |

Composition F (Controlled Release Formulation)

The composition is prepared by wet granulation of the ingredients (below) with a solution of povidone followed by the addition of magnesium stearate and compression.

mg/tablet

| | |
|---|---|
| (a) Active ingredient | 500 |
| (b) Hydroxypropylmethylcellulose (Methocel K4M Premium) | 112 |
| (c) Lactose B.P. | 53 |
| (d) Povidone B.P. | 28 |
| (e) Magnesium Stearate | 7 |
|  | 700 |

EXAMPLE 74

Capsule Compositions

Composition A

A capsule composition is prepared by admixing the ingredients of Composition D in Example 73 above and filling into a two-part hard gelatin capsule. Composition B (infra) is prepared in a similar manner.

|  | mg/capsule |
|---|---|
| Composition B |  |
| (a) Active ingredient | 250 |
| (b) Lactose B.P. | 143 |
| (c) Sodium Starch Glycollate | 25 |
| (d) Magnesium Stearate | 2 |
|  | 420 |
| Composition C |  |
| (a) Active ingredient | 250 |
| (b) Macrogol 4000 B.P. | 350 |
|  | 600 |
| Composition D |  |
| Active ingredient | 250 |
| Lecithin | 100 |
| Arachis Oil | 100 |
|  | 450 |

Capsules of composition D are prepared by dispersing the active ingredient in the lecithin and arachis oil and filling the dispersion into soft, elastic gelatin capsules.

| Composition E | mg/capsule |
|---|---|
| (a) Active ingredient | 100 |
| (b) Lactose | 300 |
| (c) Magnesium Stearate | 2 |
| (d) Sodium Lauryl Sulfate | 2 |
| (e) Sodium Starch Glycollate | 50 |
| (f) Talc, USP | 25 |
|  | 479 |

A capsule composition is prepared by micronizing the active ingredient using a GEM-T Type 1047 Jet Mill and admixing with the remaining ingredients of Composition E and filling into a two-part hard gelatin capsule.

Composition F (Controlled Release Capsule)

The following controlled release capsule composition is prepared by extruding ingredients a, b and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active ingredient | 250 |
| (b) Microcrystalline Cellulose | 125 |
| (c) Lactose B.P. | 125 |
| (d) Ethyl Cellulose | 13 |
| | 513 |

EXAMPLE 75

| Injectable Composition | |
|---|---|
| Active ingredient | 0.200 g |
| 95% Ethanol and PEG 400, 1:1 ratio | |
| Sterile water | q.s. to 10 mL |

The active ingredient is dissolved in 95% Ethanol and PEG 400 (1:1). The batch is then made up to volume with the water and filtered through a sterile micropore filter into a sterile 10 mL amber glass vial (type 1) and sealed with sterile closures and overseals.

EXAMPLE 76

| Syrup | |
|---|---|
| Active ingredient | 0.25 g |
| Sorbitol Solution | 1.50 g |
| Glycerol | 2.00 g |
| Sodium Benzoate | 0.005 g |
| Flavor, Peach 17.42.3169 | 0.0125 mL |
| Purified Water | q.s. to 5.00 mL |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE 77

| Suppository | mg/suppository |
|---|---|
| Active ingredient | 250 |
| Hard Fat, B.P. (Witepsol H15 - Dynamit NoBel) | 1770 |
| | 2020 |

One-fifth of the Witepsol H15 is melted in a steam-jacketed pan at 45° C. maximum. The active ingredient is sifted through a 200 $\mu$M sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 $\mu$M stainless steel screen and, with continuous stirring, is allowed to cool to 40° C. At a temperature of 38° C. to 40° C., 2.02 g of the mixture is filled into suitable, 2 mL plastic molds. The suppositories are allowed to cool to room temperature.

EXAMPLE 78

| Pessaries | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 79

Central Muscle Relaxant Activity

Central muscle relaxant activity of compounds of formula (I) was determined using a Straub tail test based on that described by K. O. Ellis and J. F. Carpenter, Neuropharrnacol, 13, 211 (1974).

The Straub tail test result is reported as an $ED_{50}$ in mg/kg. The $ED_{50}$ is defined as the dose of compound administered, which prevents Straub tail in 50% of mice. The compound is administered by oral gavage 60 min. prior to scoring.

The side effect potential of these compounds was determined using the mouse rotorod test as described by G. D. Novak and J. M. Zwolshei, J.Pharmacological. Methods, 10, 175 (1983). Rotorod result is reported as $ED_{50}$ in mg/kg. The $ED_{50}$ is the dose which causes 50% of the animals to fail to maintain position on a cylinder rotating at 11 r.p.m.

Antagonism of morphine-induced Straub tail reflects central muscle relaxant efficacy while failure in the rotorod test reflects sedation and incoordination. Determination of the ratio of rotorod failure to antagonism of morphine-induced Straub tail is a means of assessing side effect liability of central muscle relaxants (G. D. Novak, Drug Dev. Res., 2, 383 (1982).

| Compound of Example No. | Straub Tail p.o. $ED_{50}$, mg/kg. | Rotorod p.o. $ED_{50}$, mg/kg. | Rotorod/Straub Tail |
|---|---|---|---|
| 1 | 51 | 88 | 1.7 |
| 5 | 54 | 79 | 1.5 |

EXAMPLE 80

Anticonvulsant Activity

Anticonvulsant activity of compounds of formula (I) was determined using a method described by Mehta et al., J.Med.Chem., 24, 465 (1981).

The anticonvulsant activity is reported as an $ED_{50}$ in mg/kg. The $ED_{50}$ for protection against maximal electroshock-induced convulsions was the dose which prevented hind limb extension in 50% of the animals. The $ED_{50}$ for protection against Metrazol-induced convulsions was the dose which prevented convulsions in 50% of the animals.

| Compound of | i.p. ED$_{50}$, mg/kg (rat) | |
|---|---|---|
| Example No | MES | MET |
| 13 | 25 i.p. | 5.2 p.o. |

MES - maximal electroshock
MET - metrazol

EXAMPLE 81

Anxiolytic Activity

Anxiolytic activity of compounds of formula (I) was measured using the method of Geller and Seifter, J.Psychopharmacolgia, 1, 482 (1960) as modified by Pollard and Howard, Psychopharmacology, 62, 117 (1979). Clinically efficacious anxiolytics increase punished responding. The anxiolytic activity of the compound is reported as the lowest dose necessary to produce a significant increase in punished responding in rats(MED).

| Compound of Example No. | p.o. MED, mg/kg |
|---|---|
| 13 | 3.13 p.o. |

MED - Minimal Effective Dose

EXAMPLE 82

Antiinflammatory Activity

Compounds of formula (I) possess anti-inflammatory activity as demonstrated using a modification of the standard carrageenan pleurisy assay as described by R. Vinegar, J. F., Traux, and J. L. Selph(Pro. Soc. Exp. Biol. Med 143:711–714, 1973). The rats used in these experiments were Lewis males, weighing 160–180 g, assigned to groups consisting of 5 animals. Test compounds were given to fasted rats by oral gavage 0.5 hr prior to intrapleural injection of 50 mg carrageenan. After 4 hr, the pleural exudate was collected and the edema volume and cell number were determined. ED$_{50}$ values were estimated by linear regression analysis, and represent the doses at which a given drug produced 50% inhibition of carrageenan-induced cell accumulation and edema formation within the rat pleural cavity.

| Compound of Example No. | p.o. ED$_{50}$, mg/kg | |
|---|---|---|
| | Cells | Edema |
| 1 | 21 | 20 |
| 5 | 16 | 12 |

EXAMPLE 83

Established Adjuvant Arthritis

Compounds of formula (I) also exhibit chronic antiinflammatory activity as evidenced by inhibition of established adjuvant-induced polyarthritis in the rat. The procedures for this test have been described in detail by R. Vinegar, J. F. Truax, J. L. Selph, A. Lea, and P. R. Johnston (J. Immunopharmacol. 1:497–520, 1979). The rats used in these studies were female Lewis rats whose starting weight was 190±10 g. Arthritic rats were assigned to treatment groups consisting of six animals each. Fed rats were dosed by oral gavage starting on day 21 post adjuvant injection; therapy was continued until day 28. The incidence and severity of arthritic lesions were assessed using a modification of the scoring procedure described by H. L. F. Currey and M. Ziff (J. Exp. Med. 121:185–203, 1968). Briefly, the bilateral joints were scored for erythema, edema, and ankylosis as outlined below:

| | Arbitrary Joint Score (range) | |
|---|---|---|
| Joint Evaluated | Right | Left |
| Wrist | 0–4 | 0–4 |
| Ankle | 0–4 | 0–4 |
| Tarsus | 0–4 | 0–4 |
| Metacarpals | 0–4 | 0–4 |
| Metatarsals | 0–4 | 0–4 |

The maximal possible score per rat was 40. Experimental results were analyzed by one-way ANOVA, followed by post hoc comparisons of treatment effects versus untreated arthritic control using the Newman-Keuls test. The percent inhibition of each drug-treated group was calculated from the mean relative to the arthritic control. Compound of Example No. 5 significantly (p<0.01) lowered arthritic scores on days 22, 25, and 27 in rats with established adjuvant arthritis dosed b.i.d. with 50 mg/kg. Spleen weight and plasma fibrinogen were measured postmortem on day 27 and were also significantly reduced (p<0.01).

EXAMPLE 84

Mild Analgesia

Compounds of formula (I) possess mild analgesic activity as demonstrated using a modification of the trypsin-induced rat hind limb hyperalgesia assay as described by R. Vinegar, J. F. Truax, J. L. Selph and P. R. Johnston (J. Pharmacol. Meth., 23:51–61, 1990). The rats used in these studies were Lewis male, weighing 160–180 g. and assigned to groups consisting of 5–6 animals. Test compounds were given to fasted rats by oral gavage 0.5 hours prior to the subplantar injection of 250 mg trypsin in one hind limb. One hour later the rats were evaluated for hyperalgesia using an F-shaped mechanical force clamp on the injected hind limb metatarsal area. Latency (seconds) to the algesic response (vocalization or flight) was determined, with 4 seconds being the maximum latency allowed. ED$_{50}$ values were estimated by linear regression analysis and represent the dose at which a given drug extended the latency response to produce 50% inhibition using the formula: (4 sec.–Control Latency)–(4 sec.–Test Latency)/4 sec.–Control Latency×100.

| Compound of Example No. | p.o. ED$_{50}$, mg/kg |
|---|---|
| 5 | 4.0 |

EXAMPLE 85

Strong Analgesia

Compounds of formula (I) possess strong analgesic activity as demonstrated using the phalanges algesic assay [a modification of the trypsin-induced rat hind limb hyperalgesia assay as described by R. Vinegar, J. F. Truax, J. L. Selph and P. R. Johnston (J. Pharmacol. Meth. 23:51–61, 1990)]. The rats used in these studies were Lewis male weighing 160–180 g and assigned to groups of 5–6 animals. The phalanges algesic assay is an algesic test (no hyperalgesia) in which test compounds were given to fasted rats by oral gavage. One hour later an F-shaped mechanical force clamp was applied to the phalanges of one hind limb which initiated an algesic response(vocalization or flight). Latency (seconds) to the algesic response was determined with 3 seconds maximum allowed time. $ED_{50}$ values were estimated by linear regression analysis and represent the dose at which a given compound extended the latency response to produce 50% inhibition using the formula: (3 sec.–Control Latency)–(3 sec.–Test Latency)/3 sec.–Control Latency×100.

| Compound of Example No. | p.o. $ED_{50}$, mg/kg |
|---|---|
| 5 | 22 |

EXAMPLE 86

Toxicity Data (i) Compound of Example 1

Single doses (15, 45, 100 or 250 mg/kg) were administered by oral gavage to groups of four non-fasted male CD-1 mice (Charles River). The maximum tolerated dose was greater than 250 mg/kg as there were no deaths within the seven days post dosing.

(ii) Compound of Example 5

Single doses (5, 15, 40, 100, 250, 500 or 1000 mg/kg) were administered by oral gavage to groups of four non-fasted male CD-1 mice (Charles River). The maximum tolerated dose was greater than 1000 mg/kg as there were no deaths within the seven days post dosing.

We claim:

1. Compounds of formula (I)

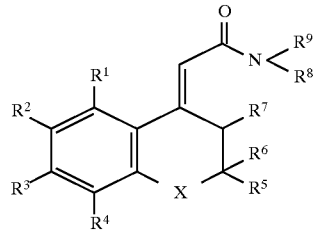

(I)

wherein
- $R^1$, $R^2$, $R^3$ and $R^4$ are each selected from hydrogen and fluoro and at least one and not more than two is fluoro;
- $R^5$ is selected from hydrogen and $C_1$–$C_4$ alkyl;
- $R^6$ is selected from hydrogen, $C_1$–$C_4$ alkyl and hydroxy; or
- $R^5$ and $R^6$ together with the ring carbon form a carbonyl group;
- $R^7$ is selected from hydrogen and hydroxy;
- $R^8$ and $R^9$ are each selected from hydrogen, $C_1$–$C_4$ alkyl and cyclo($C_3$ or $C_4$) alkyl or together with the nitrogen form a morpholino group; and
- X is selected from a bond, methylene and —O— and is always a bond or —O— when any of $R^5$, $R^6$ and $R^7$ is other than hydrogen and is always a bond when $R^5$ and $R^6$ together with the ring carbon form a carbonyl group;

and salts and solvates thereof.

2. A compound of formula (I) according to claim 1, or a pharmaceutically acceptable salt or solvate thereof, for use in the medical treatment of a mammal including a human being.

3. A pharmaceutical composition comprising a compound of formula (I) according to claim 1, or a pharmaceutically acceptable salt or solvate thereof together with an acceptable carrier therefor.

4. A method for the treatment of
   a) a condition associated with abnormally raised skeletal muscle tone;
   b) a condition associated with a convulsive state;
   c) anxiety;
   d) pain; or
   e) an inflammatory condition in a mammal, in need thereof, including a human being, the method comprising administering thereto a therapeutically effective amount of a compound of formula (I) according to claim 1 or a pharmaceutically acceptable salt or solvate thereof.

5. A process for preparing compounds of formula (I) and salts and solvates thereof which comprises:

reacting an amine of formula $NR^8R^9$ or a suitable derivative thereof with a compound of formula (II)

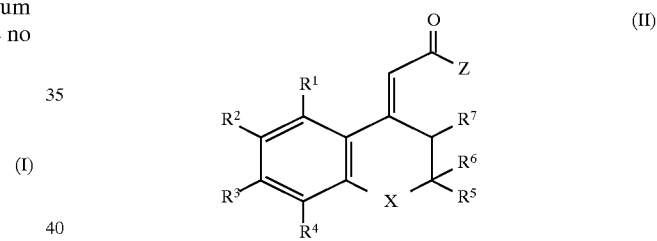

(II)

wherein Z is a leaving group and $R^1$ to $R^9$ and X are as defined in claim 1.

6. A compound according to claim 1 which is selected from the group consisting of (E)-2-(4,6,-difluoro-1-indanylidene)acetamide and (E)-2-(6-fluoro-1-indanylidene)acetamide.

7. A compound according to claim 1 which is selected from the group consisting of (E)-2-(6-fluoro-3-hydroxy-1-indanylidene)acetamide, (Z)-2-(6-fluoro-2-hydroxy-1-indanylidene)acetamide, (E)-2-(4,6-difluoro-3-hydroxy-1-indanylidene)acetamide and (Z)-2-(4,6-difluoro-2-hydroxy-1-indanylidene)acetamide.

8. A pharmaceutical composition comprising a compound of claim 6, or a pharmaceutically acceptable salt or solvate thereof, together with an acceptable carrier therefor.

9. A pharmaceutical composition comprising a composition of claim 7, or a pharmaceutically acceptable salt or solvate thereof, together with an acceptable carrier therefor.

* * * * *